(12) United States Patent
Oestergaard et al.

(10) Patent No.: US 9,057,040 B2
(45) Date of Patent: Jun. 16, 2015

(54) LACCASE VARIANTS

(75) Inventors: Lars Henrik Oestergaard, Charlottenlund (DK); Leonardo De Maria, Frederiksberg (DK); Miguel Duarte Toscano, Koebenhavn N (DK)

(73) Assignee: NOVOZYMES A/S, Bagsvaerd (DE)

( * ) Notice: Subject to any disclaimer, the term of this patent is extended or adjusted under 35 U.S.C. 154(b) by 500 days.

(21) Appl. No.: 12/935,644

(22) PCT Filed: Apr. 16, 2009

(86) PCT No.: PCT/EP2009/054554
§ 371 (c)(1),
(2), (4) Date: Sep. 30, 2010

(87) PCT Pub. No.: WO2009/127702
PCT Pub. Date: Oct. 22, 2009

(65) Prior Publication Data
US 2011/0091934 A1    Apr. 21, 2011

Related U.S. Application Data

(60) Provisional application No. 61/047,300, filed on Apr. 23, 2008, provisional application No. 61/086,939, filed on Aug. 7, 2008.

(30) Foreign Application Priority Data

Apr. 17, 2008 (EP) ..................................... 08154728
Jul. 30, 2008 (EP) ..................................... 08161508

(51) Int. Cl.
*C11D 3/386* (2006.01)
*C12N 9/02* (2006.01)

(52) U.S. Cl.
CPC ........ *C11D 3/38636* (2013.01); *C11D 3/38681* (2013.01); *C12N 9/0061* (2013.01); *C12Y 110/03002* (2013.01)

(58) Field of Classification Search
None
See application file for complete search history.

(56) References Cited

U.S. PATENT DOCUMENTS

| | | | |
|---|---|---|---|
| 7,884,066 B2 * | 2/2011 | Ting ............................... | 514/1.1 |
| 7,884,069 B2 * | 2/2011 | Schaebitz et al. ............ | 424/85.1 |
| 7,884,263 B2 * | 2/2011 | Dewey et al. ................. | 800/285 |

FOREIGN PATENT DOCUMENTS

WO    WO 2007/054034    5/2007

OTHER PUBLICATIONS

Machczynski et al., "Characterization of SLAC: a small laccase from *Streptomyces coelicolor* with unprecedented activity", Protein Science, vol. 13, No. 9, pp. 2388-2397 (2004).
Tindbaek et al., "Engineering a substrate-specific cold-adapted subtilisin", Protein Engineering, Design and Selection, vol. 17, No. 2, pp. 149-156 (2004).
Database UniProt Accession No. Q9XAL8—Abstract (1999).
Database EMBL Accession No. AL939129—Abstract (1999).
Partial search report issued in corresponding International Application No. PCT/EP2009/054554 dated Oct. 29, 2009.
Skalova et al, 2007, Acta Cryst F63, 1077-1079.

* cited by examiner

*Primary Examiner* — Hope Robinson
(74) *Attorney, Agent, or Firm* — Michael W. Krenicky

(57) ABSTRACT

The present invention relates to variants of a parent laccase. The present invention also relates to polynucleotides encoding the variant laccases and to nucleic acid constructs, vectors, and host cells comprising the polynucleotides, and methods of using the variant enzymes.

19 Claims, No Drawings

SEQUENCE LISTING

```
<160> NUMBER OF SEQ ID NOS: 40

<210> SEQ ID NO 1
<211> LENGTH: 1032
<212> TYPE: DNA
<213> ORGANISM: Streptomyces coelicolor
<220> FEATURE:
<221> NAME/KEY: CDS
<222> LOCATION: (1)..(1029)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1029)

<400> SEQUENCE: 1 atg gac agg cga ggc ttt aac cga cgg gta ctg ctg ggc ggc gcg gcc      48
Met Asp Arg Arg Gly Phe Asn Arg Arg Val Leu Leu Gly Gly Ala Ala
-30             -25                 -20                 -15 gcc gcg aca tcg ttg tcc atc gct ccg gag gtc gcg ggc gcc gcc ccc      96
Ala Ala Thr Ser Leu Ser Ile Ala Pro Glu Val Ala Gly Ala Ala Pro
            -10                 -5                  -1   1 gcg gcc aag ggg atc acc gcg agg acg gca ccg gcc ggg ggc gag gtg     144
Ala Ala Lys Gly Ile Thr Ala Arg Thr Ala Pro Ala Gly Gly Glu Val
        5                  10                  15 aga cac ctc aag atg tac gcc gag aag ctg gcg gac ggt cag atg ggc     192
Arg His Leu Lys Met Tyr Ala Glu Lys Leu Ala Asp Gly Gln Met Gly
    20                  25                  30 tac ggc ttc gag aag ggc aag gcg tcg gtc ccc ggc ccg ctg atc gag     240
Tyr Gly Phe Glu Lys Gly Lys Ala Ser Val Pro Gly Pro Leu Ile Glu
35                  40                  45                  50 gtc aac gag ggc gac acg ctg cat atc gag ttc acc aac acg atg gac     288
Val Asn Glu Gly Asp Thr Leu His Ile Glu Phe Thr Asn Thr Met Asp
                55                  60                  65 gtg cgg gcc agc ctg cac gtg cac ggc ctg gac tac gag atc tcc agc     336
Val Arg Ala Ser Leu His Val His Gly Leu Asp Tyr Glu Ile Ser Ser
            70                  75                  80 gac ggt acc gcg atg aac aag agc gac gtc gag ccc ggc ggc acc cgc     384
Asp Gly Thr Ala Met Asn Lys Ser Asp Val Glu Pro Gly Gly Thr Arg
        85                  90                  95 acc tac acc tgg cgc acc cac aaa ccg ggc cgc gac gac ggc acc         432
Thr Tyr Thr Trp Arg Thr His Lys Pro Gly Arg Arg Asp Asp Gly Thr
    100                 105                 110 tgg cgg ccg ggc agc gcg ggc tac tgg cac tac cac gac cac gtc gtc     480
Trp Arg Pro Gly Ser Ala Gly Tyr Trp His Tyr His Asp His Val Val
115                 120                 125                 130
```

```
ggc acc gaa cac ggc acc gga ggc atc cgc aac ggc ctg tac ggc ccg      528
Gly Thr Glu His Gly Thr Gly Gly Ile Arg Asn Gly Leu Tyr Gly Pro
                135                 140                 145 gtg atc gtg cgc cgc aag ggg gac gtg ctg ccg gac gcc acg cac acg      576
Val Ile Val Arg Arg Lys Gly Asp Val Leu Pro Asp Ala Thr His Thr
            150                 155                 160 atc gtc ttc aac gac atg acc atc aac aac cgc aag ccg cac acc ggc      624
Ile Val Phe Asn Asp Met Thr Ile Asn Asn Arg Lys Pro His Thr Gly
        165                 170                 175 ccc gac ttc gag gcc acc gtg ggc gac cgc gtg gag atc gtc atg atc      672
Pro Asp Phe Glu Ala Thr Val Gly Asp Arg Val Glu Ile Val Met Ile
    180                 185                 190 acg cac ggg gag tac tac cac acc ttc cac atg cac ggt cac cgc tgg      720
Thr His Gly Glu Tyr Tyr His Thr Phe His Met His Gly His Arg Trp
195                 200                 205                 210 gcg gac aac cgg acc ggc atc ctc acc ggc ccc gac gac ccg tcc cgg      768
Ala Asp Asn Arg Thr Gly Ile Leu Thr Gly Pro Asp Asp Pro Ser Arg
                215                 220                 225 gtc atc gac aac aag atc acc ggc ccg gcc gac tcc ttc ggc ttc cag      816
Val Ile Asp Asn Lys Ile Thr Gly Pro Ala Asp Ser Phe Gly Phe Gln
            230                 235                 240 atc atc gcg ggg gag ggg gtg ggc gcc ggg gcg tgg atg tac cac tgc      864
Ile Ile Ala Gly Glu Gly Val Gly Ala Gly Ala Trp Met Tyr His Cys
        245                 250                 255 cac gtc cag agc cac tcc gac atg ggc atg gtg ggg ctg ttc ctg gtg      912
His Val Gln Ser His Ser Asp Met Gly Met Val Gly Leu Phe Leu Val
    260                 265                 270 aag aag ccg gac ggc acg atc ccc ggg tac gaa ccg cac gag cac ggc      960
Lys Lys Pro Asp Gly Thr Ile Pro Gly Tyr Glu Pro His Glu His Gly
275                 280                 285                 290 ggg gcg acc gcg aag agc ggc gag agc ggg gag ccg acg ggc ggg gcg     1008
Gly Ala Thr Ala Lys Ser Gly Glu Ser Gly Glu Pro Thr Gly Gly Ala
                295                 300                 305 gcc gca cac gaa cac gag cac tga                                      1032
Ala Ala His Glu His Glu His
            310

<210> SEQ ID NO 2
<211> LENGTH: 343
<212> TYPE: PRT
<213> ORGANISM: Streptomyces coelicolor

<400> SEQUENCE: 2

Met Asp Arg Arg Gly Phe Asn Arg Arg Val Leu Leu Gly Gly Ala Ala
-30                 -25                 -20                 -15

Ala Ala Thr Ser Leu Ser Ile Ala Pro Glu Val Ala Gly Ala Ala Pro
                -10                 -5                  -1  1

Ala Ala Lys Gly Ile Thr Ala Arg Thr Ala Pro Ala Gly Gly Glu Val
            5                   10                  15

Arg His Leu Lys Met Tyr Ala Glu Lys Leu Ala Asp Gly Gln Met Gly
        20                  25                  30

Tyr Gly Phe Glu Lys Gly Lys Ala Ser Val Pro Gly Pro Leu Ile Glu
35                  40                  45                  50

Val Asn Glu Gly Asp Thr Leu His Ile Glu Phe Thr Asn Thr Met Asp
                55                  60                  65

Val Arg Ala Ser Leu His Val His Gly Leu Asp Tyr Glu Ile Ser Ser
            70                  75                  80

Asp Gly Thr Ala Met Asn Lys Ser Asp Val Glu Pro Gly Gly Thr Arg
```

```
                    85                  90                  95
Thr Tyr Thr Trp Arg Thr His Lys Pro Gly Arg Arg Asp Asp Gly Thr
    100                 105                 110

Trp Arg Pro Gly Ser Ala Gly Tyr Trp His Tyr His Asp His Val Val
115                 120                 125                 130

Gly Thr Glu His Gly Thr Gly Ile Arg Asn Gly Leu Tyr Gly Pro
                135                 140                 145

Val Ile Val Arg Arg Lys Gly Asp Val Leu Pro Asp Ala Thr His Thr
            150                 155                 160

Ile Val Phe Asn Asp Met Thr Ile Asn Asn Arg Lys Pro His Thr Gly
        165                 170                 175

Pro Asp Phe Glu Ala Thr Val Gly Asp Arg Val Glu Ile Val Met Ile
    180                 185                 190

Thr His Gly Glu Tyr Tyr His Thr Phe His Met His Gly His Arg Trp
195                 200                 205                 210

Ala Asp Asn Arg Thr Gly Ile Leu Thr Gly Pro Asp Asp Pro Ser Arg
                215                 220                 225

Val Ile Asp Asn Lys Ile Thr Gly Pro Ala Asp Ser Phe Gly Phe Gln
            230                 235                 240

Ile Ile Ala Gly Glu Gly Val Gly Ala Gly Ala Trp Met Tyr His Cys
        245                 250                 255

His Val Gln Ser His Ser Asp Met Gly Met Val Gly Leu Phe Leu Val
    260                 265                 270

Lys Lys Pro Asp Gly Thr Ile Pro Gly Tyr Glu Pro His Glu His Gly
275                 280                 285                 290

Gly Ala Thr Ala Lys Ser Gly Glu Ser Gly Glu Pro Thr Gly Gly Ala
                295                 300                 305

Ala Ala His Glu His Glu His
            310

<210> SEQ ID NO 3
<211> LENGTH: 1047
<212> TYPE: DNA
<213> ORGANISM: Streptomyces griseus
<220> FEATURE:
<221> NAME/KEY: CDS
<222> LOCATION: (1)..(1044)
<220> FEATURE:
<221> NAME/KEY: sig_peptide
<222> LOCATION: (1)..(102)
<220> FEATURE:
<221> NAME/KEY: mat_peptide
<222> LOCATION: (103)..(1044)

<400> SEQUENCE: 3 atg gac cga agg acc ttc agc cgg cgg atg ctg gtc ggt ggc gca gcc      48
Met Asp Arg Arg Thr Phe Ser Arg Arg Met Leu Val Gly Gly Ala Ala
-30                 -25                 -20 gcg gcc gcg acc ggg gtg aca tcg ttg tcg ctc ggg gcg gtg gag gcg      96
Ala Ala Ala Thr Gly Val Thr Ser Leu Ser Leu Gly Ala Val Glu Ala
                -15                 -10                 -5 agc tcg gcc gag aat ccg ccg cgt acg gcc ccg gcc ggc ggg gtg gtg     144
Ser Ser Ala Glu Asn Pro Pro Arg Thr Ala Pro Ala Gly Gly Val Val
        -1  1               5                   10 cgc cga ctg aag atg tac gcc gag aag ctg ccg aac ggc gag ctg ggc     192
Arg Arg Leu Lys Met Tyr Ala Glu Lys Leu Pro Asn Gly Glu Leu Gly
15                  20                  25                  30 tac ggc ttc gag aag ggc aag gcc tcg atc ccc ggc ccc ctc atc gag     240
Tyr Gly Phe Glu Lys Gly Lys Ala Ser Ile Pro Gly Pro Leu Ile Glu
```

```
               35                  40                  45
ctg aac gag ggc gac acg gtc cac atc gag ttc gag aac ctc acc gac        288
Leu Asn Glu Gly Asp Thr Val His Ile Glu Phe Glu Asn Leu Thr Asp
         50                  55                  60 gtc gac gcc agc ctc cac gtc cac ggg gtc gac tac gac atc gcc aac        336
Val Asp Ala Ser Leu His Val His Gly Val Asp Tyr Asp Ile Ala Asn
     65                  70                  75 gac ggc acc cgg atg aac aag agc cac gtc gag ccc ggc ggc acc cgg        384
Asp Gly Thr Arg Met Asn Lys Ser His Val Glu Pro Gly Gly Thr Arg
 80                  85                  90 acg tac acc tgg cgc acc cac gcc ccg ggc cgc cgc aag gac ggc acc        432
Thr Tyr Thr Trp Arg Thr His Ala Pro Gly Arg Arg Lys Asp Gly Thr
 95                 100                 105                 110 tac gag ccg ggc agc gcg ggc tac tgg cac tac cac gac cac gtc gtc        480
Tyr Glu Pro Gly Ser Ala Gly Tyr Trp His Tyr His Asp His Val Val
                    115                 120                 125 ggc acg gac cac ggc acc ggc ggc atc cgc aag ggg ctg tac ggg ccg        528
Gly Thr Asp His Gly Thr Gly Gly Ile Arg Lys Gly Leu Tyr Gly Pro
                130                 135                 140 gtc gtc gtg cgc cgc aag ggc gac atc ctg ccc gac cag acc tgc acg        576
Val Val Val Arg Arg Lys Gly Asp Ile Leu Pro Asp Gln Thr Cys Thr
145                 150                 155 gtc gtc ttc aac gac atg atg atc aac aac aag acg gcc cac aac agc        624
Val Val Phe Asn Asp Met Met Ile Asn Asn Lys Thr Ala His Asn Ser
160                 165                 170 gtc aac ttc gag gcc acg gtg ggt gat cgg ctc gaa ttc gtc atg atc        672
Val Asn Phe Glu Ala Thr Val Gly Asp Arg Leu Glu Phe Val Met Ile
175                 180                 185                 190 acg cac ggt gag ttc tac cac acc ttc cac atc cac ggt cac cgc tgg        720
Thr His Gly Glu Phe Tyr His Thr Phe His Ile His Gly His Arg Trp
                    195                 200                 205 gcg gac aac cgg acg ggc atc ctc acc ggc ccc gac gac ccg agc cgg        768
Ala Asp Asn Arg Thr Gly Ile Leu Thr Gly Pro Asp Asp Pro Ser Arg
                210                 215                 220 gtc atc gac aac aag atc tgc ggc ccc gcg gac tcc ttc ggc ctc cag        816
Val Ile Asp Asn Lys Ile Cys Gly Pro Ala Asp Ser Phe Gly Leu Gln
                225                 230                 235 atc atc gcg ggc gaa cgc gtg ggc gcg ggc gcc tgg atg tac cac tgt        864
Ile Ile Ala Gly Glu Arg Val Gly Ala Gly Ala Trp Met Tyr His Cys
            240                 245                 250 cac gtg cag agc cac tcc gac atg ggg atg gcc ggg ctg ctg ctg atc        912
His Val Gln Ser His Ser Asp Met Gly Met Ala Gly Leu Leu Leu Ile
255                 260                 265                 270 aag aag gcc gac ggc acc atc ccg ggc tac gaa ccg cat cac gcg gcg        960
Lys Lys Ala Asp Gly Thr Ile Pro Gly Tyr Glu Pro His His Ala Ala
                275                 280                 285 ggc ggc acg gag aag aag gcc ggg gcg aag ggc gcc ggc gcg aac gcg       1008
Gly Gly Thr Glu Lys Lys Ala Gly Ala Lys Gly Ala Gly Ala Asn Ala
                290                 295                 300 gac aag gcc gcg aag ggc gcc gcg gag cac cag cac tga                   1047
Asp Lys Ala Ala Lys Gly Ala Ala Glu His Gln His
                305                 310

<210> SEQ ID NO 4
<211> LENGTH: 348
<212> TYPE: PRT
<213> ORGANISM: Streptomyces griseus

<400> SEQUENCE: 4

Met Asp Arg Arg Thr Phe Ser Arg Arg Met Leu Val Gly Gly Ala Ala
```

```
                -30                 -25                 -20
Ala Ala Ala Thr Gly Val Thr Ser Leu Ser Leu Gly Ala Val Glu Ala
            -15                 -10                  -5

Ser Ser Ala Glu Asn Pro Pro Arg Thr Ala Pro Ala Gly Gly Val Val
 -1   1              5                  10

Arg Arg Leu Lys Met Tyr Ala Glu Lys Leu Pro Asn Gly Glu Leu Gly
 15              20                  25                  30

Tyr Gly Phe Glu Lys Gly Lys Ala Ser Ile Pro Gly Pro Leu Ile Glu
                 35                  40                  45

Leu Asn Glu Gly Asp Thr Val His Ile Glu Phe Glu Asn Leu Thr Asp
             50                  55                  60

Val Asp Ala Ser Leu His Val His Gly Val Asp Tyr Asp Ile Ala Asn
             65                  70                  75

Asp Gly Thr Arg Met Asn Lys Ser His Val Glu Pro Gly Gly Thr Arg
             80                  85                  90

Thr Tyr Thr Trp Arg Thr His Ala Pro Gly Arg Arg Lys Asp Gly Thr
 95             100                 105                 110

Tyr Glu Pro Gly Ser Ala Gly Tyr Trp His Tyr His Asp His Val Val
                115                 120                 125

Gly Thr Asp His Gly Thr Gly Gly Ile Arg Lys Gly Leu Tyr Gly Pro
             130                 135                 140

Val Val Arg Arg Lys Gly Asp Ile Leu Pro Asp Gln Thr Cys Thr
             145                 150                 155

Val Val Phe Asn Asp Met Met Ile Asn Asn Lys Thr Ala His Asn Ser
             160                 165                 170

Val Asn Phe Glu Ala Thr Val Gly Asp Arg Leu Glu Phe Val Met Ile
175                 180                 185                 190

Thr His Gly Glu Phe Tyr His Thr Phe His Ile His Gly His Arg Trp
                195                 200                 205

Ala Asp Asn Arg Thr Gly Ile Leu Thr Gly Pro Asp Asp Pro Ser Arg
             210                 215                 220

Val Ile Asp Asn Lys Ile Cys Gly Pro Ala Asp Ser Phe Gly Leu Gln
             225                 230                 235

Ile Ile Ala Gly Glu Arg Val Gly Ala Gly Trp Met Tyr His Cys
 240                 245                 250

His Val Gln Ser His Ser Asp Met Gly Met Ala Gly Leu Leu Leu Ile
255                 260                 265                 270

Lys Lys Ala Asp Gly Thr Ile Pro Gly Tyr Glu Pro His His Ala Ala
                 275                 280                 285

Gly Gly Thr Glu Lys Lys Ala Gly Ala Lys Gly Ala Gly Ala Asn Ala
             290                 295                 300

Asp Lys Ala Ala Lys Gly Ala Ala Glu His Gln His
             305                 310

<210> SEQ ID NO 5
<211> LENGTH: 1047
<212> TYPE: DNA
<213> ORGANISM: Streptomyces griseus
<220> FEATURE:
<221> NAME/KEY: CDS
<222> LOCATION: (1)..(1044)
<220> FEATURE:
<221> NAME/KEY: sig_peptide
<222> LOCATION: (1)..(102)
<220> FEATURE:
<221> NAME/KEY: mat_peptide
<222> LOCATION: (103)..(1044)
```

<400> SEQUENCE: 5

```
atg gac cga agg acc ttc agc cgg cgg atg ctg gtc ggt ggc gca gcc       48
Met Asp Arg Arg Thr Phe Ser Arg Arg Met Leu Val Gly Gly Ala Ala
-30                 -25                 -20 gcg gcc gcg acc ggg gtg aca tcg ttg tcg ctc ggg gcg gtg gag gcg       96
Ala Ala Ala Thr Gly Val Thr Ser Leu Ser Leu Gly Ala Val Glu Ala
        -15                 -10                  -5 agc tcg gcc gag aat ccg ccg cgt acg gcc ccg gcc ggc ggg gtg gtg      144
Ser Ser Ala Glu Asn Pro Pro Arg Thr Ala Pro Ala Gly Gly Val Val
 -1   1              5                  10 cgc cga ctg aag atg tac gcc gag aag ctg ccg aac ggc gag ctg ggc      192
Arg Arg Leu Lys Met Tyr Ala Glu Lys Leu Pro Asn Gly Glu Leu Gly
 15              20                  25                  30 tac ggc ttc gag aag ggc aag gcc tcg atc ccc ggc ccc ctc atc gag      240
Tyr Gly Phe Glu Lys Gly Lys Ala Ser Ile Pro Gly Pro Leu Ile Glu
                 35                  40                  45 ctg aac gag ggc gac acg gtc cac atc gag ttc aag aac ctc acc gac      288
Leu Asn Glu Gly Asp Thr Val His Ile Glu Phe Lys Asn Leu Thr Asp
             50                  55                  60 gtc gac gcc agc ctc cac gtc cac ggg gtc gac tac gac atc gcc aac      336
Val Asp Ala Ser Leu His Val His Gly Val Asp Tyr Asp Ile Ala Asn
         65                  70                  75 gac ggc acc cgg atg aac aag agc cac gtc gag ccc ggc ggc acc cgg      384
Asp Gly Thr Arg Met Asn Lys Ser His Val Glu Pro Gly Gly Thr Arg
 80                  85                  90 acg tac acc tgg cgc acc cac gcc ccg ggc cgc cgc aag gac ggc acc      432
Thr Tyr Thr Trp Arg Thr His Ala Pro Gly Arg Arg Lys Asp Gly Thr
 95                 100                 105                 110 tac gag ccg ggc agc gcg ggc tac tgg cac tac cac gac cac gtc gtc      480
Tyr Glu Pro Gly Ser Ala Gly Tyr Trp His Tyr His Asp His Val Val
                115                 120                 125 ggc acg gac cac ggc acc ggc ggc atc cgc aag ggg ctg tac ggg ccg      528
Gly Thr Asp His Gly Thr Gly Gly Ile Arg Lys Gly Leu Tyr Gly Pro
            130                 135                 140 gtc gtc gtg cgc cgc aag ggc gac atc ctg ccc gac cag acc tgc acg      576
Val Val Val Arg Arg Lys Gly Asp Ile Leu Pro Asp Gln Thr Cys Thr
        145                 150                 155 gtc gtc ttc aac gac atg atg atc aac aac aag acg gcc cac aac agc      624
Val Val Phe Asn Asp Met Met Ile Asn Asn Lys Thr Ala His Asn Ser
    160                 165                 170 gtc aac ttc gag gcc acg gtg ggt gat cgg ctc gaa ttc gtc atg atc      672
Val Asn Phe Glu Ala Thr Val Gly Asp Arg Leu Glu Phe Val Met Ile
175                 180                 185                 190 acg cac ggt gaa ttc tac cac acc ttc cac atc cac ggt cac cgc tgg      720
Thr His Gly Glu Phe Tyr His Thr Phe His Ile His Gly His Arg Trp
                195                 200                 205 gcg gac aac cgg acg ggc atc ctc acc ggc ccc gac gac ccg agc cgg      768
Ala Asp Asn Arg Thr Gly Ile Leu Thr Gly Pro Asp Asp Pro Ser Arg
            210                 215                 220 gtc atc gga caa caa gat ctg cgg ccc cgc gac tcc tac ggc ctc cag      816
Val Ile Gly Gln Gln Asp Leu Arg Pro Arg Asp Ser Tyr Gly Leu Gln
        225                 230                 235 atc atc gcg ggc gaa cgc gtg ggc gcg ggc gcc tgg atg tac cac tgt      864
Ile Ile Ala Gly Glu Arg Val Gly Ala Gly Ala Trp Met Tyr His Cys
    240                 245                 250 cac gtg cag agc cac tcc gac atg ggg atg gcc ggg ctg ctg ctg atc      912
His Val Gln Ser His Ser Asp Met Gly Met Ala Gly Leu Leu Leu Ile
255                 260                 265                 270
```

```
aag aag gcc gac ggc acc atc ccg ggc tac gaa ccg cat cac gcg gcg      960
Lys Lys Ala Asp Gly Thr Ile Pro Gly Tyr Glu Pro His His Ala Ala
                275                 280                 285 ggc ggc acg gag aag aag gcc ggg gcg aag ggc gcc ggc gcg aac gcg     1008
Gly Gly Thr Glu Lys Lys Ala Gly Ala Lys Gly Ala Gly Ala Asn Ala
        290                 295                 300 gac aag gcc gcg aag ggc gcc gcg gag cac cag cac tga                 1047
Asp Lys Ala Ala Lys Gly Ala Ala Glu His Gln His
305                 310

<210> SEQ ID NO 6
<211> LENGTH: 348
<212> TYPE: PRT
<213> ORGANISM: Streptomyces griseus

<400> SEQUENCE: 6

Met Asp Arg Arg Thr Phe Ser Arg Arg Met Leu Val Gly Gly Ala Ala
-30                 -25                 -20

Ala Ala Ala Thr Gly Val Thr Ser Leu Ser Leu Gly Ala Val Glu Ala
        -15                 -10                  -5

Ser Ser Ala Glu Asn Pro Pro Arg Thr Ala Pro Ala Gly Gly Val Val
 -1   1                  5                  10

Arg Arg Leu Lys Met Tyr Ala Glu Lys Leu Pro Asn Gly Glu Leu Gly
 15                 20                  25                  30

Tyr Gly Phe Glu Lys Gly Lys Ala Ser Ile Pro Gly Pro Leu Ile Glu
                35                  40                  45

Leu Asn Glu Gly Asp Thr Val His Ile Glu Phe Lys Asn Leu Thr Asp
                50                  55                  60

Val Asp Ala Ser Leu His Val His Gly Val Asp Tyr Asp Ile Ala Asn
 65                  70                  75

Asp Gly Thr Arg Met Asn Lys Ser His Val Glu Pro Gly Gly Thr Arg
         80                  85                  90

Thr Tyr Thr Trp Arg Thr His Ala Pro Gly Arg Arg Lys Asp Gly Thr
 95                 100                 105                 110

Tyr Glu Pro Gly Ser Ala Gly Tyr Trp His Tyr His Asp His Val Val
                115                 120                 125

Gly Thr Asp His Gly Thr Gly Gly Ile Arg Lys Gly Leu Tyr Gly Pro
                130                 135                 140

Val Val Val Arg Arg Lys Gly Asp Ile Leu Pro Asp Gln Thr Cys Thr
                145                 150                 155

Val Val Phe Asn Asp Met Met Ile Asn Asn Lys Thr Ala His Asn Ser
        160                 165                 170

Val Asn Phe Glu Ala Thr Val Gly Asp Arg Leu Glu Phe Val Met Ile
175                 180                 185                 190

Thr His Gly Glu Phe Tyr His Thr Phe His Ile His Gly His Arg Trp
                195                 200                 205

Ala Asp Asn Arg Thr Gly Ile Leu Thr Gly Pro Asp Asp Pro Ser Arg
                210                 215                 220

Val Ile Gly Gln Gln Asp Leu Arg Pro Arg Asp Ser Tyr Gly Leu Gln
                225                 230                 235

Ile Ile Ala Gly Glu Arg Val Gly Ala Gly Ala Trp Met Tyr His Cys
                240                 245                 250

His Val Gln Ser His Ser Asp Met Gly Met Ala Gly Leu Leu Leu Ile
255                 260                 265                 270

Lys Lys Ala Asp Gly Thr Ile Pro Gly Tyr Glu Pro His His Ala Ala
                275                 280                 285
```

Gly Gly Thr Glu Lys Lys Ala Gly Ala Lys Gly Ala Gly Ala Asn Ala
            290                 295                 300

Asp Lys Ala Ala Lys Gly Ala Ala Glu His Gln His
            305                 310

<210> SEQ ID NO 7
<211> LENGTH: 1008
<212> TYPE: DNA
<213> ORGANISM: Streptomyces ipomoeae
<220> FEATURE:
<221> NAME/KEY: CDS
<222> LOCATION: (1)..(1005)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1005)

<400> SEQUENCE: 7

```
atg gac agg cga ggc ttc aac cga cgg gta ctg ctg ggc ggc gcg gcc        48
Met Asp Arg Arg Gly Phe Asn Arg Arg Val Leu Leu Gly Gly Ala Ala
-30                 -25                 -20                 -15 gtc gcg aca tcg ttg tcc atc gca ccg gag acc gca ggc gcg gcc ggt        96
Val Ala Thr Ser Leu Ser Ile Ala Pro Glu Thr Ala Gly Ala Ala Gly
        -10                  -5                  -1  1 gac gcc aag ggg gtc acc gcg cgg acg gcg ccc gcc ggc ggc gag gtg       144
Asp Ala Lys Gly Val Thr Ala Arg Thr Ala Pro Ala Gly Gly Glu Val
                  5                  10                  15 aga cac atc aag atg tac gcc gag aag ctg ccc gac ggc cag atg ggc       192
Arg His Ile Lys Met Tyr Ala Glu Lys Leu Pro Asp Gly Gln Met Gly
         20                  25                  30 tac ggc ctc gag aag ggc aag gcg tcc gtt ccc ggc ccg ctg atc gag       240
Tyr Gly Leu Glu Lys Gly Lys Ala Ser Val Pro Gly Pro Leu Ile Glu
 35                  40                  45                  50 ctg aac gag ggc gac acg ctg cac atc gag ttc acg aac acc atg gac       288
Leu Asn Glu Gly Asp Thr Leu His Ile Glu Phe Thr Asn Thr Met Asp
                 55                  60                  65 gtg cgc gcc agc ctg cac gtc cac ggc ctg gac tac gag atc tcc agc       336
Val Arg Ala Ser Leu His Val His Gly Leu Asp Tyr Glu Ile Ser Ser
         70                  75                  80 gac ggc acg gcg atg aac aag agc gac gtg gag ccc ggc ggc acc cgc       384
Asp Gly Thr Ala Met Asn Lys Ser Asp Val Glu Pro Gly Gly Thr Arg
     85                  90                  95 acc tac acc tgg cgc acc cac aag ccc ggc cgc cgc gcg gac ggc acc       432
Thr Tyr Thr Trp Arg Thr His Lys Pro Gly Arg Arg Ala Asp Gly Thr
100                 105                 110 tgg cgg gcg ggc agc gcc ggt tac tgg cac tac cac gac cac gtc gtc       480
Trp Arg Ala Gly Ser Ala Gly Tyr Trp His Tyr His Asp His Val Val
115                 120                 125                 130 ggc acc gag cac ggc acc ggc ggc atc cgc aag ggc ctg tac ggc ccg       528
Gly Thr Glu His Gly Thr Gly Gly Ile Arg Lys Gly Leu Tyr Gly Pro
                135                 140                 145 gtg atc gtg cgc cgc aag ggc gac gtg ctg ccg gac gcg acg cac acc       576
Val Ile Val Arg Arg Lys Gly Asp Val Leu Pro Asp Ala Thr His Thr
        150                 155                 160 atc gtc ttc aac gac atg ctc atc aac aac cgc gcc ccg cac acc ggg       624
Ile Val Phe Asn Asp Met Leu Ile Asn Asn Arg Ala Pro His Thr Gly
    165                 170                 175 ccg aac ttc gag gcc acc gtg ggg gac cgc gtc gag atc gtc atg atc       672
Pro Asn Phe Glu Ala Thr Val Gly Asp Arg Val Glu Ile Val Met Ile
180                 185                 190
```

```
acg cac ggc gag tac tac cac acc ttc cac atg cac ggt cac cgc tgg      720
Thr His Gly Glu Tyr Tyr His Thr Phe His Met His Gly His Arg Trp
195                 200                 205                 210 gcc gac aac cgc acc ggc atg ctc acc ggc ccg gac gac ccg agc cag      768
Ala Asp Asn Arg Thr Gly Met Leu Thr Gly Pro Asp Asp Pro Ser Gln
            215                 220                 225 gtc atc gac aac aag atc acc ggg ccg gcg gac tcc ttc ggc ttc cag      816
Val Ile Asp Asn Lys Ile Thr Gly Pro Ala Asp Ser Phe Gly Phe Gln
        230                 235                 240 atc atc gcg ggg gag ggg gtg ggc gcc ggg gcg tgg atg tac cac tgc      864
Ile Ile Ala Gly Glu Gly Val Gly Ala Gly Ala Trp Met Tyr His Cys
    245                 250                 255 cat gtg cag agc cac tcc gac atg ggg atg gtg ggc ctg ttc ctg gtg      912
His Val Gln Ser His Ser Asp Met Gly Met Val Gly Leu Phe Leu Val
260                 265                 270 aag aag ccg gac ggc acg atc ccc ggc tac gac ccg cac gag cac gcg      960
Lys Lys Pro Asp Gly Thr Ile Pro Gly Tyr Asp Pro His Glu His Ala
275                 280                 285                 290 cac ggc ggc ggc gaa ccg acc gcg gac gcg ccc gcg cac cag cac tga     1008
His Gly Gly Gly Glu Pro Thr Ala Asp Ala Pro Ala His Gln His
            295                 300                 305
```

<210> SEQ ID NO 8
<211> LENGTH: 335
<212> TYPE: PRT
<213> ORGANISM: Streptomyces ipomoeae

<400> SEQUENCE: 8

```
Met Asp Arg Arg Gly Phe Asn Arg Arg Val Leu Leu Gly Gly Ala Ala
-30                 -25                 -20                 -15

Val Ala Thr Ser Leu Ser Ile Ala Pro Glu Thr Ala Gly Ala Ala Gly
            -10                 -5                  -1  1

Asp Ala Lys Gly Val Thr Ala Arg Thr Ala Pro Ala Gly Gly Glu Val
            5                   10                  15

Arg His Ile Lys Met Tyr Ala Glu Lys Leu Pro Asp Gly Gln Met Gly
        20                  25                  30

Tyr Gly Leu Glu Lys Gly Lys Ala Ser Val Pro Gly Pro Leu Ile Glu
35                  40                  45                  50

Leu Asn Glu Gly Asp Thr Leu His Ile Glu Phe Thr Asn Thr Met Asp
                55                  60                  65

Val Arg Ala Ser Leu His Val His Gly Leu Asp Tyr Glu Ile Ser Ser
            70                  75                  80

Asp Gly Thr Ala Met Asn Lys Ser Asp Val Glu Pro Gly Gly Thr Arg
        85                  90                  95

Thr Tyr Thr Trp Arg Thr His Lys Pro Gly Arg Arg Ala Asp Gly Thr
    100                 105                 110

Trp Arg Ala Gly Ser Ala Gly Tyr Trp His Tyr His Asp His Val Val
115                 120                 125                 130

Gly Thr Glu His Gly Thr Gly Gly Ile Arg Lys Gly Leu Tyr Gly Pro
                135                 140                 145

Val Ile Val Arg Arg Lys Gly Asp Val Leu Pro Asp Ala Thr His Thr
            150                 155                 160

Ile Val Phe Asn Asp Met Leu Ile Asn Asn Arg Ala Pro His Thr Gly
        165                 170                 175

Pro Asn Phe Glu Ala Thr Val Gly Asp Arg Val Glu Ile Val Met Ile
    180                 185                 190
```

-continued

Thr His Gly Glu Tyr Tyr His Thr Phe His Met Gly His Arg Trp
195                 200                 205                 210

Ala Asp Asn Arg Thr Gly Met Leu Thr Gly Pro Asp Asp Pro Ser Gln
                215                 220                 225

Val Ile Asp Asn Lys Ile Thr Gly Pro Ala Asp Ser Phe Gly Phe Gln
            230                 235                 240

Ile Ile Ala Gly Glu Gly Val Gly Ala Gly Trp Met Tyr His Cys
        245                 250                 255

His Val Gln Ser His Ser Asp Met Gly Met Val Gly Leu Phe Leu Val
    260                 265                 270

Lys Lys Pro Asp Gly Thr Ile Pro Gly Tyr Asp Pro His Glu His Ala
275                 280                 285                 290

His Gly Gly Gly Glu Pro Thr Ala Asp Ala Pro Ala His Gln His
                295                 300                 305

<210> SEQ ID NO 9
<211> LENGTH: 31
<212> TYPE: DNA
<213> ORGANISM: Artificial Sequence
<220> FEATURE:
<223> OTHER INFORMATION: Primer 1

<400> SEQUENCE: 9
aggatccacc atggacaggc gaggctttaa c          31

<210> SEQ ID NO 10
<211> LENGTH: 31
<212> TYPE: DNA
<213> ORGANISM: Artificial Sequence
<220> FEATURE:
<223> OTHER INFORMATION: Primer 2

<400> SEQUENCE: 10
actcgagtca gtgctcgtgt tcgtgtgcgg c          31

<210> SEQ ID NO 11
<211> LENGTH: 33
<212> TYPE: DNA
<213> ORGANISM: Artificial Sequence
<220> FEATURE:
<223> OTHER INFORMATION: Primer 3

<400> SEQUENCE: 11
accggccccg acgacgcctc ccgggtcatc gac          33

<210> SEQ ID NO 12
<211> LENGTH: 33
<212> TYPE: DNA
<213> ORGANISM: Artificial Sequence
<220> FEATURE:
<223> OTHER INFORMATION: Primer 4

<400> SEQUENCE: 12
ggccccgacg acccgaaccg ggtcatcgac aac          33

<210> SEQ ID NO 13
<211> LENGTH: 33
<212> TYPE: DNA
<213> ORGANISM: Artificial Sequence
<220> FEATURE:
<223> OTHER INFORMATION: Primer 5

<400> SEQUENCE: 13

```
gttgtcgatg acccggttcg ggtcgtcggg gcc                            33
```

<210> SEQ ID NO 14
<211> LENGTH: 28
<212> TYPE: DNA
<213> ORGANISM: Artificial Sequence
<220> FEATURE:
<223> OTHER INFORMATION: Primer 6

<400> SEQUENCE: 14

```
cagagccact ccgacgccgg catggtgg                                 28
```

<210> SEQ ID NO 15
<211> LENGTH: 38
<212> TYPE: DNA
<213> ORGANISM: Artificial Sequence
<220> FEATURE:
<223> OTHER INFORMATION: Primer 7

<400> SEQUENCE: 15

```
gatcacgcac ggggagcatt accacacctt ccacatgc                      38
```

<210> SEQ ID NO 16
<211> LENGTH: 33
<212> TYPE: DNA
<213> ORGANISM: Artificial Sequence
<220> FEATURE:
<223> OTHER INFORMATION: Primer 8

<400> SEQUENCE: 16

```
atcgtcttca acgacaccat caacaaccgc aag                           33
```

<210> SEQ ID NO 17
<211> LENGTH: 22
<212> TYPE: DNA
<213> ORGANISM: Artificial Sequence
<220> FEATURE:
<223> OTHER INFORMATION: Primer 9

<400> SEQUENCE: 17

```
cttcaacgac gcgaccatca ac                                       22
```

<210> SEQ ID NO 18
<211> LENGTH: 34
<212> TYPE: DNA
<213> ORGANISM: Artificial Sequence
<220> FEATURE:
<223> OTHER INFORMATION: Primer 10

<400> SEQUENCE: 18

```
ccactgccac gtccaggaac actccgacat gggc                          34
```

<210> SEQ ID NO 19
<211> LENGTH: 34
<212> TYPE: DNA
<213> ORGANISM: Artificial Sequence
<220> FEATURE:
<223> OTHER INFORMATION: Primer 11

<400> SEQUENCE: 19

```
gatcacgcac gggtcgtact accacacctt ccac                          34
```

<210> SEQ ID NO 20
<211> LENGTH: 34
<212> TYPE: DNA
<213> ORGANISM: Artificial Sequence

```
<220> FEATURE:
<223> OTHER INFORMATION: Primer 12

<400> SEQUENCE: 20
ccactgccac gtccagcagc actccgacat gggc                              34

<210> SEQ ID NO 21
<211> LENGTH: 34
<212> TYPE: DNA
<213> ORGANISM: Artificial Sequence
<220> FEATURE:
<223> OTHER INFORMATION: Primer 13

<400> SEQUENCE: 21
ccactgccac gtccagaagc actccgacat gggc                              34

<210> SEQ ID NO 22
<211> LENGTH: 28
<212> TYPE: DNA
<213> ORGANISM: Artificial Sequence
<220> FEATURE:
<223> OTHER INFORMATION: Primer 14

<400> SEQUENCE: 22
cagagccact ccgactgggg catggtgg                                     28

<210> SEQ ID NO 23
<211> LENGTH: 33
<212> TYPE: DNA
<213> ORGANISM: Artificial Sequence
<220> FEATURE:
<223> OTHER INFORMATION: Primer 15

<400> SEQUENCE: 23
gacaaccgga ccggcgccct caccggcccc gac                               33

<210> SEQ ID NO 24
<211> LENGTH: 33
<212> TYPE: DNA
<213> ORGANISM: Artificial Sequence
<220> FEATURE:
<223> OTHER INFORMATION: Primer 16

<400> SEQUENCE: 24
gacaaccgga ccggcctcct caccggcccc gac                               33

<210> SEQ ID NO 25
<211> LENGTH: 33
<212> TYPE: DNA
<213> ORGANISM: Artificial Sequence
<220> FEATURE:
<223> OTHER INFORMATION: Primer 17

<400> SEQUENCE: 25
ggcgccgggg cgtggctcta ccactgccac gtc                               33

<210> SEQ ID NO 26
<211> LENGTH: 33
<212> TYPE: DNA
<213> ORGANISM: Artificial Sequence
<220> FEATURE:
<223> OTHER INFORMATION: Primer 18

<400> SEQUENCE: 26
cacgtcgtcg gcaccgccca cggcaccgga ggc                               33
```

<210> SEQ ID NO 27
<211> LENGTH: 34
<212> TYPE: DNA
<213> ORGANISM: Artificial Sequence
<220> FEATURE:
<223> OTHER INFORMATION: Primer 19

<400> SEQUENCE: 27
gatcgaggtc aacgagtccg acacgctgca tatc         34

<210> SEQ ID NO 28
<211> LENGTH: 38
<212> TYPE: DNA
<213> ORGANISM: Artificial Sequence
<220> FEATURE:
<223> OTHER INFORMATION: Primer 20

<400> SEQUENCE: 28
gatcacgcac gggtcgtggt accacacctt ccacatgc     38

<210> SEQ ID NO 29
<211> LENGTH: 33
<212> TYPE: DNA
<213> ORGANISM: Artificial Sequence
<220> FEATURE:
<223> OTHER INFORMATION: Primer 21

<400> SEQUENCE: 29
aggatccacc atggaccgaa ggaccttcag ccg          33

<210> SEQ ID NO 30
<211> LENGTH: 25
<212> TYPE: DNA
<213> ORGANISM: Artificial Sequence
<220> FEATURE:
<223> OTHER INFORMATION: Primer 22

<400> SEQUENCE: 30
actcgagtca gtgctggtgc tccgc                   25

<210> SEQ ID NO 31
<211> LENGTH: 34
<212> TYPE: DNA
<213> ORGANISM: Artificial Sequence
<220> FEATURE:
<223> OTHER INFORMATION: Primer 23

<400> SEQUENCE: 31
catgatcacg cacggtagtt tctaccacac cttc         34

<210> SEQ ID NO 32
<211> LENGTH: 33
<212> TYPE: DNA
<213> ORGANISM: Artificial Sequence
<220> FEATURE:
<223> OTHER INFORMATION: Primer 24

<400> SEQUENCE: 32
cactgtcacg tgcagacgca ctccgacatg ggg          33

<210> SEQ ID NO 33
<211> LENGTH: 31
<212> TYPE: DNA
<213> ORGANISM: Artificial Sequence
<220> FEATURE:
<223> OTHER INFORMATION: Primer SLAC_fwd_BamHI -continued

<400> SEQUENCE: 33
aggattcacc atggacaggc gaggctttaa c							31

<210> SEQ ID NO 34
<211> LENGTH: 31
<212> TYPE: DNA
<213> ORGANISM: Artificial Sequence
<220> FEATURE:
<223> OTHER INFORMATION: Primer SLAC_rev_XhoI

<400> SEQUENCE: 34
actcgagtca gtgctcgtgt tcgtgtgcgg c							31

<210> SEQ ID NO 35
<211> LENGTH: 28
<212> TYPE: DNA
<213> ORGANISM: Artificial Sequence
<220> FEATURE:
<223> OTHER INFORMATION: Primer BamHI_trunc_SLAC_fwd

<400> SEQUENCE: 35
aggatccacc atggcccccg cggccaag							28

<210> SEQ ID NO 36
<211> LENGTH: 22
<212> TYPE: DNA
<213> ORGANISM: Artificial Sequence
<220> FEATURE:
<223> OTHER INFORMATION: Primer pHUda_fwd

<400> SEQUENCE: 36
ccttcacgga gaaacccag cg							22

<210> SEQ ID NO 37
<211> LENGTH: 43
<212> TYPE: DNA
<213> ORGANISM: Artificial Sequence
<220> FEATURE:
<223> OTHER INFORMATION: Primer A_ory_sign_SLAC_rev

<400> SEQUENCE: 37
gatccccttg gccgcggggg ccccgagggc cagcttcccc agc							43

<210> SEQ ID NO 38
<211> LENGTH: 21
<212> TYPE: DNA
<213> ORGANISM: Artificial Sequence
<220> FEATURE:
<223> OTHER INFORMATION: Primer sign_SLAC_fwd

<400> SEQUENCE: 38 gccccgcgg ccaaggggat c							21

<210> SEQ ID NO 39
<211> LENGTH: 33
<212> TYPE: DNA
<213> ORGANISM: Artificial Sequence
<220> FEATURE:
<223> OTHER INFORMATION: Primer SgL_fwd_ BamHI

<400> SEQUENCE: 39
aggatccacc atggaccgaa ggaccttcag ccg							33

<210> SEQ ID NO 40

```
<211> LENGTH: 25
<212> TYPE: DNA
<213> ORGANISM: Artificial Sequence
<220> FEATURE:
<223> OTHER INFORMATION: Primer SgL_rev_XhoI

<400> SEQUENCE: 40
actcgagtca gtgctggtgc tccgc                                             25
```

LACCASE VARIANTS

CROSS-REFERENCE TO RELATED APPLICATIONS

This application is a 35 U.S.C. 371 national application of PCT/EP2009/054554 filed Apr. 16, 2009, which claims priority or the benefit under 35 U.S.C. 119 of European application nos. 08154728.3 filed Apr. 17, 2008 and 08161508.0 filed Jul. 30, 2008 and U.S. provisional application nos. 61/047,300 filed Apr. 23, 2008 and 61/086,939 filed Aug. 7, 2008, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to variants of a laccase, polynucleotides encoding the variants, methods of producing the variants, and methods of using the variants.

2. Description of the Related Art

A small laccase from *Streptomyces coelicolor* was disclosed in Machczynski et al., "Characterization of SLAC: a small laccase from *Streptomyces coelicolor* with unprecedented activity", *Protein Science* (2004), Vol. 13, pp. 2388-2397. Certain properties of this laccase were later disclosed in WO 2007/054034. No publications exist disclosing variants of this enzyme.

It is an object of the present invention to provide variants of the *Streptomyces coelicolor* laccase, and similar laccases, with improved properties compared to their parent enzyme.

SUMMARY OF THE INVENTION

The present invention relates to isolated variants of a parent laccase, comprising a substitution at one or more (several) positions corresponding to positions M168, E198, Y199, Y200, S262, M266, H74, A120, G121, Y122, W123, H124, D212, N213, R214, D223, P224, S225, R226, V227, I228, D229, N230, K231, I232, T233 A236, D237, S238, F239, S43, S81, S82, S101, M33, M65, M87, M255, T8, T11, T56, T62, T64, T97, T99, T101, T114, T132, T136, T160, T162, T169, T177, T180, T184, T215, T219, A29P, K39P, D111P, K152P, T8P, A9P, I80P, A86P, M87P, I232P, M255P, V260P, T56P, H58P, K106D, K106E, K152D, K152E, D30E, H176R, G96S, G54S, G54T, L143S, L143T, K41N, R68N, E79N, S262N, G54N, E60N, T62N, G95N, T97N, T99N, D158N, E182N, I217N, and D278N of the mature polypeptide of SEQ ID NO: 2, wherein the variants have laccase activity.

The present invention also relates to isolated polypeptides having laccase activity, wherein the amino acid sequences of the polypeptides differ from the mature polypeptide of SEQ ID NO:2 at one or more (several) positions corresponding to positions M168, E198, Y199, Y200, S262, M266, H74, A120, G121, Y122, W123, H124, D212, N213, R214, D223, P224, S225, R226, V227, I228, D229, N230, K231, I232, T233 A236, D237, S238, F239, S43, S81, S82, S101, M33, M65, M87, M255, T8, T11, T56, T62, T64, T97, T99, T101, T114, T132, T136, T160, T162, T169, T177, T180, T184, T215, T219, A29P, K39P, D111P, K152P, T8P, A9P, I80P, A86P, M87P, I232P, M255P, V260P, T56P, H58P, K106D, K106E, K152D, K152E, D30E, H176R, G96S, G54S, G54T, L143S, L143T, K41N, R68N, E79N, S262N, G54N, E60N, T62N, G95N, T97N, T99N, D158N, E182N, I217N, and D278N of the mature polypeptide of SEQ ID NO: 2.

The present invention also relates to isolated polynucleotides encoding the variant laccases or polypeptides having laccase activity, nucleic acid constructs, vectors, and host cells comprising the polynucleotides, and methods of producing a variant of a parent laccase or a polypeptide having laccase activity.

The present invention also relates to compositions and uses thereof, which will be apparent from the following paragraphs.

DETAILED DESCRIPTION OF THE INVENTION

The present invention relates to isolated variants of a parent laccase, comprising a substitution at one or more (several) positions corresponding to positions M168, E198, Y199, Y200, S262, M266, H74, A120, G121, Y122, W123, H124, D212, N213, R214, D223, P224, S225, R226, V227, I228, D229, N230, K231, I232, T233 A236, D237, S238, F239, S43, S81, S82, S101, M33, M65, M87, M255, T8, T11, T56, T62, T64, T97, T99, T101, T114, T132, T136, T160, T162, T169, T177, T180, T184, T215, T219, A29P, K39P, D111P, K152P, T8P, A9P, I80P, A86P, M87P, I232P, M255P, V260P, T56P, H58P, K106D, K106E, K152D, K152E, D30E, H176R, G96S, G54S, G54T, L143S, L143T, K41N, R68N, E79N, S262N, G54N, E60N, T62N, G95N, T97N, T99N, D158N, E182N, I217N, and D278N of the mature polypeptide of SEQ ID NO: 2, wherein the variant has laccase activity.

DEFINITIONS

Laccase activity: The term "laccase activity" is defined herein as covered by enzyme classification EC 1.10.3.2, or a similar activity, such as a catechol oxidase activity (EC 1.10.3.1), o-aminophenol oxidase activity (EC 1.10.3.4), or bilirubin oxidase activity (EC 1.3.3.5), that catalyzes the oxidation of a substrate using molecular oxygen. For purposes of the present invention, laccase activity is determined by oxidation of syringaldazin under aerobic conditions. The violet colour produced is measured at 530 nm. The analytical conditions are 19 µM syringaldazin, 23 mM Tris/maleate buffer, pH 7.5, 30° C., and 1 min. reaction time.

One laccase unit (LAMU) is the amount of enzyme that catalyses the conversion of 1.0 mmole syringaldazin per minute at these conditions.

Variant: The term "variant" is defined herein as a polypeptide having laccase activity comprising an alteration, such as a substitution, insertion, and/or deletion, of one or more (several) amino acid residues at one or more (several) specific positions of the mature polypeptide of SEQ ID NO: 2 or amino acids 9 to 293 of SEQ ID NO: 2. The altered polynucleotide is obtained through human intervention by modification of the polynucleotide sequence disclosed in SEQ ID NO: 1; or a homologous sequence thereof.

Wild-Type Enzyme: The term "wild-type" laccase denotes a laccase expressed by a naturally occurring microorganism, such as a bacterial, yeast, or filamentous fungus found in nature.

Parent Enzyme: The term "parent" laccase as used herein means a laccase to which a modification, e.g., substitution(s), insertion(s), deletion(s), and/or truncation(s), is made to produce the enzyme variants of the present invention. This term also refers to the polypeptide with which a variant is compared and aligned. The parent may be a naturally occurring (wild-type) polypeptide or a variant. For instance, the parent polypeptide may be a variant of a naturally occurring polypeptide which has been modified or altered in the amino acid sequence. A parent may also be an allelic variant, which is a polypeptide encoded by any of two or more alternative forms of a gene occupying the same chromosomal locus.

Isolated variant or polypeptide: The term "isolated variant" or "isolated polypeptide" as used herein refers to a variant or a polypeptide that is isolated from a source. In one aspect, the variant or polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure variant or polypeptide: The term "substantially pure variant" or "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure variant or polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The variants and polypeptides of the present invention are preferably in a substantially pure form. This can be accomplished, for example, by preparing the variant or polypeptide by well-known recombinant methods or by classical purification methods.

Mature polypeptide: The term "mature polypeptide" is defined herein as a polypeptide having laccase activity that is in its final form following translation and any post-translational modifications, such as N-terminal processing, C-terminal truncation, glycosylation, phosphorylation, etc. In one aspect, the mature polypeptide is amino acids 1 to 313 of SEQ ID NO: 2 based on the SignalP 3.0 computer software for Gram positive bacteria (please refer to Bendtsen et al., "Improved Prediction of Signal Peptides: SignalP 3.0", *J. Mol. Biol.* (2004) 340, pp. 783-795) that predicts amino acids −30 to −1 of SEQ ID NO: 2 are a signal peptide.

Mature polypeptide coding sequence: The term "mature polypeptide coding sequence" is defined herein as a nucleotide sequence that encodes a mature polypeptide having laccase activity. In one aspect, the mature polypeptide coding sequence is nucleotides 91 to 1029 of SEQ ID NO: 1 based on the SignalP 3.0 computer software for Gram positive bacteria, that predicts nucleotides 1 to 90 of SEQ ID NO: 1 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—no brief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—no brief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted polypeptide that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Streptomyces coelicolor* laccase.

Polypeptide fragment: The term "polypeptide fragment" is defined herein as a polypeptide having one or more (several) amino acids deleted from the amino and/or carboxyl terminus of the mature polypeptide; or a homologous sequence thereof; wherein the fragment has laccase activity. In one aspect, a fragment contains at least 300 amino acid residues, more preferably at least 290 amino acid residues, and most preferably at least 280 amino acid residues of the mature polypeptide or a homologous sequence thereof.

Subsequence: The term "subsequence" is defined herein as a polynucleotide sequence having one or more (several) nucleotides deleted from the 5' and/or 3' end of the mature polypeptide coding sequence; or a homologous sequence thereof; wherein the subsequence encodes a polypeptide fragment having laccase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In one aspect, the isolated polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered polypeptide production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Nucleic acid construct: The term "nucleic acid construct" as used herein refers to a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" is defined herein as a characteristic associated with a variant that is improved compared to the parent laccase. Such improved properties include, but are not limited to, thermal activity, pH activity, thermostability, and oxidative stability.

Improved thermal activity: The term "improved thermal activity" is defined herein as a variant enzyme displaying an alteration of the temperature-dependent activity profile of a laccase variant at a specific temperature relative to the temperature-dependent activity profile of the parent laccase. The thermal activity value provides a measure of the enzyme's efficiency in performing catalysis of an oxidative reaction over a range of temperatures. A laccase has a specific temperature range wherein the polypeptide is stable and retains its enzymatic activity, but becomes less stable and thus less active with increasing temperature. Furthermore, the initial rate of a reaction catalyzed by a laccase can be accelerated by an increase in temperature that is measured by determining thermal activity of a variant. A more thermoactive variant will lead to an increase in the rate of oxidation, decreasing the time required and/or decreasing the enzyme concentration required for oxidation. Alternatively, a variant with a reduced thermal activity will catalyze an oxidative reaction at a temperature lower than the temperature optimum of the parent enzyme defined by the temperature-dependent activity profile of the parent.

Improved thermostability: The term "improved thermostability" is defined herein as a variant enzyme displaying retention of enzymatic activity after a period of incubation at elevated temperature relative to the parent enzyme. Such a variant may or may not display an altered thermal activity profile relative to the parent. For example, a variant may have an improved ability to refold following incubation at elevated temperature relative to the parent.

In one aspect, the thermal activity of the variant laccase is at least 1.5-fold, preferably at least 2-fold, more preferably at least 5-fold, most preferably at least 7-fold, and even most preferably at least 10-fold more thermally active than the parent enzyme when residual activity is compared using syringaldazine as substrate.

Improved oxidative stability: The term "improved oxidative stability" is defined herein as a variant enzyme displaying retention of enzymatic activity after a period of incubation in the presence of an oxidative agent, either naturally occurring or synthetic, which reduce the enzymatic activity of the parent enzyme. Improved oxidative stability may also result in variants better able to catalyze a reaction in the presence of such agents. In particular, the oxidative stability may be improved towards radicals formed by oxidation of a mediator.

Conventions for Designation of Variants

For purposes of the present invention, the amino acid sequence of the laccase disclosed in SEQ ID NO: 2 is used to determine the corresponding amino acid residue in another laccase. The amino acid sequence of another laccases is aligned with the amino acid sequence of the laccase disclosed in SEQ ID NO: 2, and based on the alignment the amino acid position number corresponding to any amino acid residue in the amino acid sequence of the laccase disclosed in SEQ ID NO: 2 can be determined.

An alignment of polypeptide sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). An alignment of DNA sequences may be done using the polypeptide alignment as a template, replacing the amino acids with the corresponding codon from the DNA sequence.

Pairwise sequence comparison algorithms in common use are adequate to detect similarities between polypeptide sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous polypeptides with the same fold and similar biological function have often diverged to the point where traditional sequence-based comparison fails to detect their relationship (Lindahl and Elofsson, 2000, *J. Mol. Biol.* 295: 613-615). Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide of interest has one or more (several) representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide of interest, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33:88-96) or combinatorial extension (Shindyalov and Bourne, 1998, Protein Eng. 11:739-747), and implementations of these algorithms can additionally be utilized to query structure databases with a structure of interest in order to discover possible structural homologs (e.g. Holm and Park, 2000, Bioinformatics 16:566-567). These structural alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the various laccase variants of the present invention, the nomenclature described below is adapted for ease of reference. In all cases, the accepted IUPAC single letter or triple letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411 Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, new inserted amino acid. Accordingly the insertion of lysine after glycine at position 195 is designated "Gly195GlyLys" or "G195GK". Multiple insertions of amino acids are designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would thus be:

| Parent | Variant |
|--------|---------|
| 195    | 195 195a 195b |
| G      | G-K-A   |

Parent Laccases

In the present invention, the parent laccase is (a) a polypeptide comprising an amino acid sequence having at least 70% identity with the mature polypeptide of SEQ ID NO: 2 or amino acids 9 to 293 of SEQ ID NO: 2; (b) a polypeptide encoded by a polynucleotide that hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); or (c) a polypeptide encoded by a polynucleotide comprising a nucleotide sequence having at least 70% identity with the mature polypeptide coding sequence of SEQ ID NO: 1. Examples of parent laccases are shown in SEQ ID NO: 4, SEQ ID NO: 6 and SEQ ID NO: 8.

In a first aspect, the parent laccases comprise an amino acid sequence having a degree of identity to the mature polypeptide of SEQ ID NO: 2 of at least 70%, preferably at least 75%, more preferably at least 80%, more preferably at least 85%, even more preferably at least 90%, most preferably at least 95%, and even most preferably at least 96%, at least 97%, at least 98%, or at least 99%, which have laccase activity (hereinafter "homologous polypeptides"). In one aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2 or amino acids 9 to 293 of SEQ ID NO: 2.

Substantially homologous parent laccases may have one or more (several) amino acid substitutions, deletions and/or insertions. These changes are preferably of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type laccase. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

The parent laccase preferably comprises the amino acid sequence of SEQ ID NO: 2 or an allelic variant thereof; or a fragment thereof having laccase activity. In one aspect, the parent laccase comprises the amino acid sequence of SEQ ID NO: 2. In another aspect, the parent laccase comprises the mature polypeptide of SEQ ID NO: 2. In another aspect, the parent laccase comprises amino acids 1 to 313 of SEQ ID NO: 2, or an allelic variant thereof; or a fragment thereof having laccase activity. In another aspect, the parent laccase comprises amino acids 1 to 313 of SEQ ID NO: 2. In another aspect, the parent laccase consists of the amino acid sequence of SEQ ID NO: 2 or an allelic variant thereof; or a fragment thereof having laccase activity. In another aspect, the parent laccase consists of the amino acid sequence of SEQ ID NO: 2. In another aspect, the parent laccase consists of the mature polypeptide of SEQ ID NO: 2. In another aspect, the parent laccase consists of amino acids 1 to 313 of SEQ ID NO: 2 or an allelic variant thereof; or a fragment thereof having laccase activity. In another aspect, the parent laccase consists of amino acids 1 to 313 of SEQ ID NO: 2.

A fragment of the mature polypeptide of SEQ ID NO: 2 is a polypeptide having one or more (several) amino acids deleted from the amino and/or carboxyl terminus of this amino acid sequence. Preferably, a fragment contains at least 300 amino acid residues, more preferably at least 200 amino acid residues, and most preferably at least 100 amino acid residues.

In a second aspect, the parent laccases are encoded by polynucleotides that hybridize under medium stringency conditions, preferably medium-high stringency conditions, more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). The subsequence may encode a polypeptide fragment having laccase activity. In one aspect, the complementary strand is the full-length complementary strand of the mature polypeptide coding sequence of SEQ ID NO: 1.

A subsequence of the mature polypeptide coding sequence of SEQ ID NO: 1, or a homolog thereof, is a nucleotide sequence where one or more (several) nucleotides have been deleted from the 5'- and/or 3'-end. Preferably, a subsequence contains at least 900 nucleotides, more preferably at least 600 nucleotides, and most preferably at least 300 nucleotides.

The parent enzymes may also be allelic variants of the polypeptides that have laccase activity.

The polynucleotide of SEQ ID NO: 1; or a subsequence thereof; as well as the amino acid sequence of SEQ ID NO: 2; or a fragment thereof; may be used to design nucleic acid probes to identify and clone DNA encoding parent laccases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA library prepared from such other organisms may be screened for DNA that hybridizes with the probes described above and encodes a parent laccase. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is used in a Southern blot. For purposes of the present invention, hybridization indicates that the polynucleotide hybridizes to a labeled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 91 to 1029 of SEQ ID NO:

1. In another aspect, the nucleic acid probe is a polynucleotide sequence that encodes the polypeptide of SEQ ID NO: 2, or a subsequence thereof. In another aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the parent laccase is encoded by a polynucleotide comprising or consisting of a nucleotide sequence having a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. In one aspect, the mature polypeptide coding sequence is nucleotides 91 to 1029 of SEQ ID NO: 1.

The parent laccase may be obtained from microorganisms of any genus. For purposes of the present invention, the term "obtained from" as used herein in connection with a given source shall mean that the parent laccase encoded by a polynucleotide is produced by the source or by a cell in which the polynucleotide from the source has been inserted. In one aspect, the parent laccase is secreted extracellularly.

The parent laccase may be a bacterial laccase. For example, the laccase may be a Gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* laccase, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* laccase.

In one aspect, the parent laccase is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* laccase.

In another aspect, the parent laccase is a *Streptococcus equisimilis, Streptococcus pyogenes, Streptococcus uberis,* or *Streptococcus equi* subsp. *Zooepidemicus* laccase.

In another aspect, the polypeptide is a *Streptomyces achromogenes, Streptomyces* avermitilis, *Streptomyces coelicolor, Streptomyces griseus,* or *Streptomyces lividans* laccase.

The parent laccase may be a fungal laccase. In another aspect, the fungal laccase is a yeast laccase such as a *Candida, Kluyveromyces, Pichia, Saccharomyces, Schizosaccharomyces,* or *Yarrowia* laccase. In another aspect, the fungal laccase is a filamentous fungal laccase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* laccase.

In another aspect, the parent laccase is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* laccase.

In another aspect, the parent laccase is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* laccase.

In another aspect, the parent laccase is a *Streptomyces coelicolor* laccase, and most preferably the *Streptomyces coelicolor* laccase of SEQ ID NO: 2 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent laccase may also be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The polynucleotide encoding a laccase may then be derived by similarly screening a genomic or cDNA library of another microorganism or mixed DNA sample. Once a polynucleotide encoding a laccase has been detected with suitable probe(s) as described herein, the sequence may be isolated or cloned by utilizing techniques that are known to those of ordinary skill in the art (see, e.g., J. Sambrook, E. F. Fritsch, and T. Maniatus, 1989, *Molecular Cloning, A Laboratory Manual*, 2d edition, Cold Spring Harbor, N.Y.). As defined herein, an "isolated" laccase is a polypeptide that is essentially free of other non-laccase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The parent laccase can also include fused polypeptides or cleavable fusion polypeptides in which another polypeptide is fused at the N-terminus or the C-terminus of the polypeptide or fragment thereof. A fused polypeptide is produced by fusing a polynucleotide (or a portion thereof) encoding another polypeptide to a polynucleotide (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Preparation of Variants

Variants of a parent laccase can be prepared according to any mutagenesis procedure known in the art, such as site-directed mutagenesis, synthetic gene construction, semi-synthetic gene construction, random mutagenesis, shuffling, etc.

Site-directed mutagenesis is a technique in which one or several mutations are created at a defined site in a polynucleotide molecule encoding the parent laccase. The technique can be performed in vitro or in vivo.

Synthetic gene construction entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., *Nature* 432:1050-1054) and similar technologies wherein olgionucleotides are synthesized and assembled upon photo-programmable microfluidic chips.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent laccase and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, for example, Scherer and Davis, 1979, *Proc. Natl. Acad. Sci. USA* 76: 4949-4955; and Barton et al., 1990, *Nucleic Acids Research* 18: 7349-4966.

Site-directed mutagenesis can be accomplished in vivo by methods known in the art. See, for example, U.S. Patent Application Publication 2004/0171154; Storici et al., 2001, *Nature Biotechnology* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants of a parent laccase.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204) and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide fragments may then be shuffled.

Variants

The functional unit of *Streptomyces coelicolor* laccase (SLAC) shown in SEQ ID NO:2 is a trimer (see Example 2), which associate in a highly symmetrical manner. Because of this multimerization, a variant designed to change one amino acid in one monomer will also change it in both of the two other monomers; because of the high symmetry, the changes will occur at equivalent positions in the other monomers. The variants of the present invention were designed by studying the (unpublished) three-dimensional structure of the enzyme (the functional unit).

Improving Enzyme Reactivity and/or Changing the pH Activity Profile

Variants aiming to improve the enzyme reactivity have been designed along two main lines. First, solvent exposed residues in the vicinity of the T1 copper site have been identified and changed in order to improve/facilitate the binding of substrate. Second, the routes for incoming oxygen and leaving water have been identified and improved. The residues having a high impact on the activity of the enzyme will also be of importance for changing the pH activity profile.

The enzyme has three T1 coppers—one per monomer. Three loops located in the vicinity of each of the T1 coppers are key for the binding of the molecules to be oxidized. These loops include residues H126-Y144, N166-D180, H196-H201 and C258-V269. The most preferred positions in these loops are M168, E198, Y199, Y200, S262 and M266. Experimental evidence shows that M168A, M168G, Y199W, M266A, M168A/E198S/S262E, M168A/E198S/S262Q and M168A/E198S/S262K are substantially improved as compared to the wild type using methyl syringate, PPT and TEMPO as substrates (see Example 4).

In the laccase reaction mechanism, four one-electron oxidations of substrate occur at the T1 site on the protein surface. This mechanism is coupled to a four-electron reduction of dioxygen ($O_2$) to water ($H_2O$), which occurs at the internal trinuclear T2/T2 cluster.

This results in a lot of traffic to/from the trinuclear internal copper site. The route the electrons will follow is thought to be via "protein elements" joining the histidines coordinating the T1 copper site to the ones coordinating the T3 copper sites. Therefore, dioxygen must be able to reach the trinuclear internal copper site from the surface, and water must be able to leave after the electron-transfer has occurred. This traffic takes place through channels and cavities in the enzyme, which connects the surface and the internal copper sites. The residues flanking the channels/cavities and the copper sites are important for the speed of getting dioxygen and water in and out of the enzyme, and for the reaction rate of the enzyme. These residues can also be used to change the activity of the enzyme at different pH values.

The three monomers of the SLAC enzyme pack together leaving a large central cavity inside. The residues flanking the large internal cavity include H74, A120, G121, Y122, W123, H124, D212, N213, R214, D223, P224, S225, R226, V227, I228, D229, N230, K231, I232, T233 A236, D237, S238 and F239. The entrance of the cavity is at residue P224. The closest residues to the trinuclear copper cluster are H74, H124 and D229. In particular, D229 separates this large cavity from a small cavity just behind the T2 copper site. Experimental evidence shows that P224A and S225N are substantially improved as compared to the wild type using methyl syringate, PPT and TEMPO as substrates (see Example 4).

The following residues atoms contributing to the small cavity just behind the T2 copper: H74, G75, L76, D77, Y78, H206, G207, H208, R209 and D229. This cavity is well buried inside the protein and can only be accessed from the large central cavity at residue D229; or from a route, which starts on the surface of the enzyme at residue I217 and ends at residue R209.

One of the two T3 coppers in each monomer is separated from the protein surface by residues M87, E133, H134, M255 and V269.

Accordingly, the invention includes variants of a parent laccase, which comprise a substitution at one or more (several) positions corresponding to positions H74, G75, L76, D77, Y78, H206, G207, H208, R209, A120, G121, Y122, W123, H124, D212, N213, R214, D223, P224, S225, R226, V227, I228, D229, N230, K231, I232, T233, A236, D237, S238 and F239 of SEQ ID NO: 2, wherein the variant having laccase activity comprises an amino acid sequence having a degree of identity of at least 70%, preferably at least 75%, more preferably at least 80%, more preferably at least 85%, even more preferably at least 90%, most preferably at least 95%, and even most preferably at least about 97% to the amino acid sequence of the parent laccase.

Thermostability

Variants having improved thermostability are based on specific selected proline substitutions, introduction of selected disulfide bonds, and optimization of charged residues.

The suggested proline substitutions include: A29P, K39P, D111P, K152P, T8P, A9P, I80P, A86P, M87P, I232P, M255P, V260P, T56P, and/or H58P.

Recent experimental results show that optimization of charge-charge interactions on the surface of proteins can be a useful strategy in the design of thermostable enzymes. This was done using the three-dimensional SLAC structure, and the positions considered unsuitable for the substitutions were discarded. The suggested substitutions include: K106D, K106E, K152D, K152E, D30E, H176R, and/or G96S. Accordingly, the invention includes variants of a parent laccase, which comprise a substitution at one or more (several) positions corresponding to positions A29P, K39P, D111P, K152P, T8P, A9P, I80P, A86P, M87P, I232P, M255P, V260P, T56P, H58P, K106D, K106E, K152D, K152E, D30E, H176R, and G96S of SEQ ID NO: 2, wherein the variant having laccase activity comprises an amino acid sequence having a degree of identity of at least 70%, preferably at least 75%, more preferably at least 80%, more preferably at least 85%, even more preferably at least 90%, most preferably at least 95%, and even most preferably at least about 97% to the amino acid sequence of the parent laccase.

Oxidative Stability

The oxidized compounds (such as mediators) produced by the laccase may act on surface exposed oxidation prone residues of the enzyme, and thus harming its activity. In particular serine, methionine, threonine and tryptophan residues will, to different extent, suffer from this. Using the three-dimensional SLAC structure, we have identified the following residues, which should be changed to other appropriate—not prone to oxidation—residues: S43, S81, S82, S101, S225, S262, M33, M65, M87, M168, M266, M255, T8, T11, T56, T62, T64, T97, T99, T101, T114, T132, T136, T160, T162, T169, T177, T180, T184, T215 and T219. Accordingly, the invention includes variants of a parent laccase, which comprise a substitution at one or more (several) positions corresponding to positions S43, S81, S82, S101, S225, S262, M33, M65, M87, M168, M266, M255, T8, T11, T56, T62, T64, T97, T99, T101, T114, T132, T136, T160, T162, T169, T177, T180, T184, T215 and T219 of SEQ ID NO: 2, wherein the variant having laccase activity comprises an amino acid sequence having a degree of identity of at least 70%, preferably at least 75%, more preferably at least 80%, more preferably at least 85%, even more preferably at least 90%, most preferably at least 95%, and even most preferably at least about 97% to the amino acid sequence of the parent laccase.

Glycosylation Sites

Asparagine linked glycosylation in eukaryotes occurs at the Asn-Xaa-Ser/Thr sequon. The effect of glycosylation upon protein stability is system dependent. In this case, variants introducing new glycosylation sites have been designed. All the N-glycosylation sequons present (NXS and NXT) or amenable to be made (NXY, XYS and XYT) were examined in the context of the structure and those clearly incompatible with the sequon surroundings were eliminated. The resulting suggested substitutions include: G54S, G54T, L143S, L143T, K41N, R68N, E79N, S262N, G54N, E60N, T62N, G95N, T97N, T99N, D158N, E182N, I217N, and/or D278N. Accordingly, the invention includes variants of a parent laccase, which comprise a substitution at one or more (several)

positions corresponding to positions G54S, G54T, L143S, L143T, K41N, R68N, E79N, S262N, G54N, E60N, T62N, G95N, T97N, T99N, D158N, E182N, I217N, and D278N of SEQ ID NO: 2, wherein the variant having laccase activity comprises an amino acid sequence having a degree of identity of at least 70%, preferably at least 75%, more preferably at least 80%, more preferably at least 85%, even more preferably at least 90%, most preferably at least 95%, and even most preferably at least about 97% to the amino acid sequence of the parent laccase.

In the present invention, the isolated variants of a parent laccase comprise a substitution at one or more (several) positions corresponding to positions 168, 198, 199, 200, 262, and 266 of SEQ ID NO: 2, wherein the variant having laccase activity comprises an amino acid sequence having a degree of identity of at least 70%, preferably at least 75%, more preferably at least 80%, more preferably at least 85%, even more preferably at least 90%, most preferably at least 95%, and even most preferably at least about 97% to the amino acid sequence of the parent laccase.

In one aspect, the number of amino acid substitutions in the variants of the present invention may comprise 10 substitutions, preferably 9 substitutions, more preferably 8 substitutions, even more preferably 7 substitutions, even more preferably 6 substitutions, even more preferably 5 substitutions, even more preferably 4 substitutions, even more preferably 3 substitutions, most preferably 2 substitutions, and in particular 1 substitution. In another aspect, the number of amino acid substitutions in the variants of the present invention consists of preferably 4 substitutions, more preferably 3 substitutions, even more preferably 2, and most preferably 1 substitution.

In one aspect, a variant of a parent laccase comprises a substitution at one or more (several) positions corresponding to positions 168, 198, 199, 200, 262, and 266. In another aspect, a variant of a parent laccase comprises substitutions at two or more positions corresponding to positions 168, 198, 199, 200, 262, and 266. In another aspect, a variant of a parent laccase comprises substitutions at three or more positions corresponding to positions 168, 198, 199, 200, 262, and 266. In another aspect, a variant of a parent laccase comprises substitutions at positions corresponding to positions 168, 198, 199, 200, 262, and 266. In another aspect, the variant comprises one or more (several) substitutions selected from the group consisting of M168A, M168G, E198S, S262E, S262Q, and S262K of the mature polypeptide of SEQ ID NO: 2.

In one aspect, the variant comprises a substitution at a position corresponding to position 168. In another aspect, the variant comprises a substitution at a position corresponding to position 168 with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises Ala or Gly as a substitution at a position corresponding to position 168. In another aspect, the variant comprises the substitution M168A or M168G of the mature polypeptide of SEQ ID NO: 2.

In another aspect, the variant comprises a substitution at a position corresponding to position 198. In another aspect, the variant comprises a substitution at a position corresponding to position 198 with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises Ser as a substitution at a position corresponding to position 198. In another aspect, the variant comprises the substitution E198S of the mature polypeptide of SEQ ID NO: 2.

In another aspect, the variant comprises a substitution at a position corresponding to position 199. In another aspect, the variant comprises a substitution at a position corresponding to position 199 with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises Trp as a substitution at a position corresponding to position 199. In another aspect, the variant comprises the substitution Y199W of the mature polypeptide of SEQ ID NO: 2.

In another aspect, the variant comprises a substitution at a position corresponding to position 200. In another aspect, the variant comprises a substitution at a position corresponding to position 200 with Ala, Arg, Asn, Asp, Cys, Gln, Glu, Gly, His, Ile, Leu, Lys, Met, Phe, Pro, Ser, Thr, Trp, Tyr, or Val.

In one aspect, the variant comprises a substitution at a position corresponding to position 262. In another aspect, the variant comprises a substitution at a position corresponding to position 262 with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises Glu, Gln or Lys as a substitution at a position corresponding to position 262. In another aspect, the variant comprises the substitution S262E, S262Q or S262K of the mature polypeptide of SEQ ID NO: 2.

In another aspect, the variant comprises a substitution at a position corresponding to position 266. In another aspect, the variant comprises a substitution at a position corresponding to position 266 with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises Ala as a substitution at a position corresponding to position 266. In another aspect, the variant comprises the substitution M266A of the mature polypeptide of SEQ ID NO: 2.

In another aspect, the variant comprises substitutions at positions corresponding to positions 168 and 198. In another aspect, the variant comprises substitutions at positions corresponding to positions 168 and 198 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 168 and 199. In another aspect, the variant comprises substitutions at positions corresponding to positions 168 and 199 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 168 and 200. In another aspect, the variant comprises substitutions at positions corresponding to positions 168 and 200 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 198 and 199. In another aspect, the variant comprises substitutions at positions corresponding to positions 198 and 199 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 198 and 200. In another aspect, the variant comprises substitutions at positions corresponding to positions 198 and 200 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 199 and 200. In another aspect, the variant comprises substitutions at positions corresponding to positions 199 and 200 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 168, 198, and 199. In another aspect, the variant comprises substitutions at positions corresponding to positions 168, 198, and 199 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 168, 199, and 200. In another aspect, the variant comprises substitutions at positions corresponding to positions 168, 199, and 200 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 198, 199, and 200. In another aspect, the variant comprises substitutions at positions corresponding to positions 198, 199, and 200 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 168, 198, and 200. In another aspect, the variant comprises substitutions at positions corresponding to positions 168, 198, and 200 with Ala, Arg, Asn, Asp, Cys, Gln, Glu, Gly, His, Ile, Leu, Lys, Met, Phe, Pro, Ser, Thr, Trp, Tyr, or Val.

In another aspect, the variant comprises substitutions at positions corresponding to positions 168, 198, 199, and 200. In another aspect, the variant comprises substitutions at positions corresponding to positions 168, 198, 199, and 200 with Ala, Arg, Asn, Asp, Cys, Gln, Glu, Gly, His, Ile, Leu, Lys, Met, Phe, Pro, Ser, Thr, Trp, Tyr, or Val.

Polynucleotides

The present invention also relates to polynucleotides that encode the variants of the invention.

In one aspect, the invention relates to isolated polynucleotides that encode variants of a parent laccase, wherein the polynucleotides encode laccase variants comprising a substitution at one or more (several) positions corresponding to positions M168, E198, Y199, Y200, S262, M266, H74, A120, G121, Y122, W123, H124, D212, N213, R214, D223, P224, S225, R226, V227, I228, D229, N230, K231, I232, T233, A236, D237, S238, F239, S43, S81, S82, S101, M33, M65, M87, M255, T8, T11, T56, T62, T64, T97, T99, T101, T114, T132, T136, T160, T162, T169, T177, T180, T184, T215, T219, A29P, K39P, D111P, K152P, T8P, A9P, 180P, A86P, M87P, 1232P, M255P, V260P, T56P, H58P, K106D, K106E, K152D, K152E, D30E, H176R, G96S, G54S, G54T, L143S, L143T, K41N, R68N, E79N, S262N, G54N, E60N, T62N, G95N, T97N, T99N, D158N, E182N, I217N, and D278N of SEQ ID NO: 2, wherein the parent laccase is (a) a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 97% identity with the mature polypeptide of SEQ ID NO: 2; (ii) a polypeptide encoded by a polynucleotide that hybridizes under preferably low, more preferably low-medium, more preferably medium, even more preferably medium-high, most preferably high, or even most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii), wherein the variant has laccase activity.

Nucleic Acid Constructs

The present invention also relates to nucleic acid constructs comprising a polynucleotide encoding a laccase variant of the present invention operably linked to one or more (several) control sequences that direct the expression of the coding sequence in a suitable host cell under conditions compatible with the control sequences.

An isolated polynucleotide encoding a laccase variant of the present invention may be manipulated in a variety of ways to provide for expression of the variant. Manipulation of the polynucleotide prior to its insertion into a vector may be desirable or necessary depending on the expression vector. The techniques for modifying polynucleotides utilizing recombinant DNA methods are well known in the art.

The control sequence may be an appropriate promoter sequence, which is recognized by a host cell for expression of the polynucleotide. The promoter sequence contains transcriptional control sequences that mediate the expression of the variant laccase. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarose gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP),

*Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the variant laccase. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the variant laccase. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a variant laccase and directs the encoded polypeptide into the cell's secretory pathway. The 5'-end of the coding sequence of the polynucleotide may inherently contain a signal peptide coding region naturally linked in translation reading frame with the segment of the coding region that encodes the secreted variant laccase. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant laccase. However, any signal peptide coding region that directs the expressed polypeptide into the secretory pathway of a host cell of choice may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that codes for an amino acid sequence positioned at the amino terminus of a variant laccase. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the variant laccase relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant laccase would be operably linked with the regulatory sequence.

Expression Vectors

The present invention also relates to recombinant expression vectors comprising a polynucleotide encoding a variant laccase of the present invention, a promoter, and transcriptional and translational stop signals. The various nucleotide and control sequences described above may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of a laccase variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain substantially pure laccase variants.

Host Cells

The present invention also relates to recombinant host cells, comprising a polynucleotide encoding a variant laccase, which are advantageously used in the recombinant production of the variant. A vector comprising a polynucleotide of the present invention is introduced into a host cell so that the vector is maintained as a chromosomal integrant or as a self-replicating extra-chromosomal vector as described earlier. The choice of a host cell will to a large extent depend upon the gene encoding the polypeptide and its source.

The host cell may be any cell useful in the recombinant production of a variant laccase, e.g., a prokaryote or a eukaryote.

The prokaryotic host cell may be any Gram positive bacterium or a Gram negative bacterium. Gram positive bacteria include, but are not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but are not limited to, *E. coli*,

*Pseudomonas, Salmonella, Campylobacter, Helicobacter, Flavobacterium, Fusobacterium, Ilyobacter, Neisseria,* and *Ureaplasma.*

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

In one aspect, the bacterial host cell is a *Bacillus amyloliquefaciens, Bacillus lentus, Bacillus licheniformis, Bacillus stearothermophilus* or *Bacillus subtilis* cell. In another aspect, the bacterial host cell is a *Bacillus amyloliquefaciens* cell. In another aspect, the bacterial host cell is a *Bacillus clausii* cell. In another aspect, the bacterial host cell is a *Bacillus licheniformis* cell. In another aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis,* and *Streptococcus equi* subsp. *Zooepidemicus* cells.

In one aspect, the bacterial host cell is a *Streptococcus equisimilis* cell. In another aspect, the bacterial host cell is a *Streptococcus pyogenes* cell. In another aspect, the bacterial host cell is a *Streptococcus uberis* cell. In another aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans* cells.

In one aspect, the bacterial host cell is a *Streptomyces achromogenes* cell. In another aspect, the bacterial host cell is a *Streptomyces avermitilis* cell. In another aspect, the bacterial host cell is a *Streptomyces coelicolor* cell. In another aspect, the bacterial host cell is a *Streptomyces griseus* cell. In another aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In one aspect, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In another aspect, the yeast host cell is a *Candida, Hansenula, Kluyveromyces, Pichia, Saccharomyces, Schizosaccharomyces,* or *Yarrowia* cell.

In another aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another aspect, the yeast host cell is a *Kluyveromyces lactis* cell. In another aspect, the yeast host cell is a *Yarrowia lipolytica* cell.

In another aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In another aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In another aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulo-* sum, *Fusarium trichothecioides*, or *Fusarium venenatum* cell. In another aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a laccase variant, comprising: (a) cultivating a host cell of the present invention under conditions suitable for the expression of the variant; and (b) recovering the variant from the cultivation medium.

In the production methods of the present invention, the host cells are cultivated in a nutrient medium suitable for production of the laccase variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

In an alternative aspect, the laccase variant is not recovered, but rather a host cell of the present invention expressing a variant is used as a source of the variant.

The laccase variant may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein in the Examples.

The resulting laccase variant may be recovered by methods known in the art. For example, the polypeptide may be recovered from the nutrient medium by conventional procedures including, but not limited to, collection, centrifugation, filtration, extraction, spray-drying, evaporation, or precipitation.

A laccase variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure laccase variants.

Other Polypeptides Having Laccase Activity

The present invention also relates to isolated polypeptides having laccase activity, wherein the amino acid sequences of the polypeptides differ from SEQ ID NO: 2 at one or more (several) positions corresponding to positions M168, E198, Y199, Y200, S262, M266, H74, A120, G121, Y122, W123, H124, D212, N213, R214, D223, P224, S225, R226, V227, I228, D229, N230, K231, I232, T233 A236, D237, S238, F239, S43, S81, S82, S101, M33, M65, M87, M255, T8, T11, T56, T62, T64, T97, T99, T101, T114, T132, T136, T160, T162, T169, T177, T180, T184, T215, T219, A29P, K39P, D111P, K152P, T8P, A9P, 180P, A86P, M87P, 232P, M255P, V260P, T56P, H58P, K106D, K106E, K152D, K152E, D30E, H176R, G96S, G54S, G54T, L143S, L143T, K41N, R68N, E79N, S262N, G54N, E60N, T62N, G95N, T97N, T99N, D158N, E182N, I217N, and D278N of SEQ ID NO: 2.

In one aspect, the amino acid sequence of the polypeptide differs from the mature polypeptide of SEQ ID NO: 2 by 10 amino acids, preferably 9 amino acids, more preferably 8 amino acids, more preferably 7 amino acids, more preferably 6 amino acids, more preferably 5 amino acids, more preferably 4 amino acids, even more preferably 3 amino acids, most preferably 2 amino acids, and in particular 1 amino acid.

In one aspect, the amino acid sequence of the polypeptide differs from SEQ ID NO: 2 at one or more (several) positions corresponding to positions M168, E198, Y199, Y200, S262, M266, H74, A120, G121, Y122, W123, H124, D212, N213, R214, D223, P224, S225, R226, V227, I228, D229, N230, K231, I232, T233 A236, D237, S238, F239, S43, S81, S82, S101, M33, M65, M87, M255, T8, T11, T56, T62, T64, T97, T99, T101, T114, T132, T136, T160, T162, T169, T177, T180, T184, T215, T219, A29P, K39P, D111P, K152P, T8P, A9P, 180P, A86P, M87P, I232P, M255P, V260P, T56P, H58P, K106D, K106E, K152D, K152E, D30E, H176R, G96S, G54S, G54T, L143S, L143T, K41N, R68N, E79N, S262N, G54N, E60N, T62N, G95N, T97N, T99N, D158N, E182N, I217N, and D278N.

The isolated polypeptides have one or more (several) improved properties compared to the polypeptide of SEQ ID NO: 2, wherein the improved properties are selected from the group consisting of thermal activity, thermostability, pH activity, substrate specificity, and oxidative stability, as described herein.

The present invention also relates to isolated polynucleotides encoding such polypeptides, nucleic acid constructs, expression vectors, and host cells comprising the polynucleotides, and methods of producing the polypeptides having laccase activity, according to the same disclosure herein for laccase variants.

Plants

The present invention also relates to a transgenic plant, plant part, or plant cell that has been transformed with a polynucleotide encoding a variant laccase or polypeptide of the present invention so as to express and produce the variant or polypeptide in recoverable quantities. The a variant or polypeptide may be recovered from the plant or plant part. Alternatively, the plant or plant part containing the recombinant a variant or polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a a variant or polypeptide of the present invention may be constructed in accordance with methods known in the art. In short, the plant or plant cell is constructed by incorporating one or more (several) expression constructs encoding a a variant or polypeptide of the present invention into the plant host genome and propagating the resulting modified plant or plant cell into a transgenic plant or plant cell.

Conveniently, the expression construct is a nucleic acid construct that comprises a nucleic acid sequence encoding a a variant or polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the a variant or polypeptide is desired to be expressed. For example, the expression of the gene encoding a a variant or polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 13: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For example, the promoter enhancer element may be an intron that is placed between the promoter and the polynucleotide encoding a polypeptide of the present invention. Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art.

Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a a variant or polypeptide of the present invention comprising (a) cultivating a transgenic plant or a plant cell comprising a nucleic acid sequence encoding a a variant or polypeptide having laccase activity of the present invention under conditions conducive for production of the variant or polypeptide; and (b) recovering the a variant or polypeptide.

Enhancing Agent

An enhancing agent may be used with the polypeptides having laccase activity to improve the effect of the methods of the invention. Enhancing agents are also referred to as mediators, because they mediate, or enhance, the electron transfer between the laccase and the substrate. Enhancing agents acting as electron donors for the polypeptides having laccase activity include both inorganic and organic compounds known in the art. Several examples of such enhancing agents are shown below.

The enhancing agent may be selected from the group consisting of aliphatic, cyclo-aliphatic, heterocyclic or aromatic compounds containing the moiety >N—OH. In a preferred embodiment of the invention the enhancing agent is a compound of the general formula I:

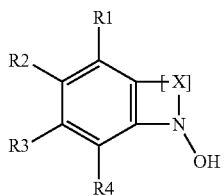

wherein $R^1$, $R^2$, $R^3$, $R^4$ are individually selected from the group consisting of hydrogen, halogen, hydroxy, formyl, carboxy and salts and esters thereof, amino, nitro, $C_{1-12}$-alkyl, $C_{1-6}$-alkoxy, carbonyl($C_{1-12}$-alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_{1-12}$-alkyl, $C_{1-6}$-alkoxy, carbonyl ($C_{1-12}$-alkyl), aryl, in particular phenyl, sulfo, aminosulfonyl, carbamoyl, phosphono, phosphonooxy, and salts and esters thereof; [X] represents a group selected from (—N=N—), (—N=CR$^6$—)$_m$, (—CR$^6$=N—)$_m$, (—CR$^7$=CR$^8$—)$_m$, (—CR$^6$=N—NR$^7$—), (—N=N—CHR$^6$—), (—N=CR$^6$—NR$^7$—), (—N=CR$^6$—CHR$^7$—), (—CR$^6$=N—CHR$^7$—), (—CR$^6$=CR$^7$—NR$^8$—), and (—CR$^6$=CR$^7$—CHR$^8$—), wherein $R^6$, $R^7$, and $R^8$ independently of each other are selected from H, OH, NH$_2$, COOH, SO$_3$H, $C_{1-6}$-alkyl, NO$_2$, CN, Cl, Br, F, CH$_2$OCH$_3$, OCH$_3$, and COOCH$_3$; and m is 1 or 2.

The term "$C_{1-n}$-alkyl" wherein n can be from 2 through 12, as used herein, represent a branched or straight alkyl group having from one to the specified number of carbon atoms. Typical $C_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl and the like.

In a more preferred embodiment of the invention the enhancing agent is a compound of the general formula II:

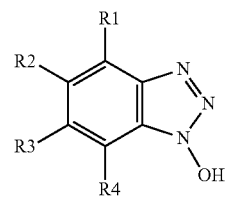

wherein $R^1$, $R^2$, $R^3$, $R^4$ are individually selected from the group consisting of hydrogen, halogen, hydroxy, formyl, carboxy and salts and esters thereof, amino, nitro, $C_{1-12}$-alkyl, $C_{1-6}$-alkoxy, carbonyl($C_{1-12}$-alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_{1-12}$-alkyl, $C_{1-6}$-alkoxy, carbonyl ($C_{1-12}$-alkyl), aryl, in particular phenyl, sulfo, aminosulfonyl, carbamoyl, phosphono, phosphonooxy, and salts and esters thereof.

The enhancing agent may also be a salt or an ester of formula I or II.

Further preferred enhancing agents are oxoderivatives and N-hydroxy derivatives of heterocyclic compounds and oximes of oxo- and formyl-derivatives of heterocyclic compounds, said heterocyclic compounds including five-membered nitrogen-containing heterocycles, in particular pyrrol, pyrazole and imidazole and their hydrogenated counterparts (e.g. pyrrolidine) as well as triazoles, such as 1,2,4-triazole; six-membered nitrogen-containing heterocycles, in particular mono-, di- and triazinanes (such as piperidine and piperazine), morpholine and their unsaturated counterparts (e.g. pyridine and pyrimidine); and condensed heterocycles containing the above heterocycles as substructures, e.g. indole, benzothiazole, quinoline and benzoazepine.

Examples of preferred enhancing agent from these classes of compounds are pyridine aldoximes; N-hydroxypyrrolidinediones such as N-hydroxysuccinimide and N-hydroxyphthalimide; 3,4-dihydro-3-hydroxybenzo[1,2,3]triazine-4-one; formaldoxime trimer (N,N',N"-trihydroxy-1,3,5-triazinane); and violuric acid (1,3-diazinane-2,4,5,6-tetrone-5-oxime).

Still further enhancing agents which may be applied in the invention include oximes of oxo- and formyl-derivatives of aromatic compounds, such as benzoquinone dioxime and salicylaldoxime (2-hydroxybenzaldehyde oxime), and N-hydroxyamides and N-hydroxyanilides, such as N-hydroxyacetanilide.

Preferred enhancing agents are selected from the group consisting of 1-hydroxybenzotriazole; 1-hydroxybenzotriazole hydrate; 1-hydroxybenzotriazole sodium salt; 1-hydroxybenzotriazole potassium salt; 1-hydroxybenzotriazole lithium salt; 1-hydroxybenzotriazole ammonium salt; 1-hydroxybenzotriazole calcium salt; 1-hydroxybenzotriazole magnesium salt; and 1-hydroxybenzotriazole-6-sulphonic acid.

A particularly preferred enhancing agent is 1-hydroxybenzotriazole.

All the specifications of N-hydroxy compounds above are understood to include tautomeric forms such as N-oxides whenever relevant.

Another preferred group of enhancing agents comprises a —CO—NOH— group and has the general formula III:

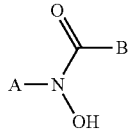

in which A is:

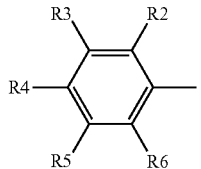

and B is the same as A; or B is H or $C_{1-12}$-alkyl, said alkyl may contain hydroxy, ester or ether groups (e.g. wherein the ether oxygen is directly attached to A-N(OH)C=O—, thus including N-hydroxy carbamic acid ester derivatives), and R2, R3, R4, R5 and R6 independently of each other are H, OH, $NH_2$, COOH, $SO_3H$, $C_{1-8}$-alkyl, acyl, $NO_2$, CN, Cl, Br, F, $CF_3$, NOH—CO-phenyl, CO—NOH-phenyl, $C_{1-6}$—CO—NOH-A, CO—NOH-A, COR12, phenyl-CO—NOH-A, OR7, NR8R9, COOR10, or NOH—CO—R11, wherein R7, R8, R9, R10, R11 and R12 are $C_{1-12}$-alkyl or acyl.

R2, R3, R4, R5 and R6 of A are preferably H, OH, $NH_2$, COOH, $SO_3H$, $C_{1-3}$-alkyl, acyl, $NO_2$, CN, Cl, Br, F, $CF_3$, NOH—CO-phenyl, CO—NOH-phenyl, COR12, OR7, NR8R9, COOR10, or NOH—CO—R11, wherein R7, R8 and R9 are $C_{1-3}$-alkyl or acyl, and R10, R11 and R12 are $C_{1-3}$-alkyl; more preferably R2, R3, R4, R5 and R6 of A are H, OH, $NH_2$, COOH, $SO_3H$, $CH_3$, acyl, $NO_2$, CN, Cl, Br, F, $CF_3$, CO—NOH-phenyl, $COCH_3$, OR7, NR8R9, or $COOCH_3$, wherein R7, R8 and R9 are $CH_3$ or $COCH_3$; even more preferably R2, R3, R4, R5 and R6 of A are H, OH, COOH, $SO_3H$, $CH_3$, acyl, $NO_2$, CN, Cl, Br, F, CO—NOH-phenyl, $OCH_3$, $COCH_3$, or $COOCH_3$; and in particular R2, R3, R4, R5 and R6 of A are H, OH, COOH, $SO_3H$, $CH_3$, $NO_2$, CN, Cl, Br, CO—NOH-phenyl, or $OCH_3$.

R2, R3, R4, R5 and R6 of B are preferably H, OH, $NH_2$, COOH, $SO_3H$, $C_{1-3}$-alkyl, acyl, $NO_2$, CN, Cl, Br, F, $CF_3$, NOH—CO-phenyl, CO—NOH-phenyl, COR12, OR7, NR8R9, COOR10, or NOH—CO—R11, wherein R7, R8 and R9 are $C_{1-3}$-alkyl or acyl, and R10, R11 and R12 are $C_{1-3}$-alkyl; more preferably R2, R3, R4, R5 and R6 of B are H, OH, $NH_2$, COOH, $SO_3H$, $CH_3$, acyl, $NO_2$, CN, Cl, Br, F, $CF_3$, CO—NOH-phenyl, $COCH_3$, OR7, NR8R9, or $COOCH_3$, wherein R7, R8 and R9 are $CH_3$ or $COCH_3$; even more preferably R2, R3, R4, R5 and R6 of B are H, OH, COOH, $SO_3H$, $CH_3$, acyl, $NO_2$, CN, Cl, Br, F, CO—NOH-phenyl, $OCH_3$, $COCH_3$, or $COOCH_3$; and in particular R2, R3, R4, R5 and R6 of B are H, OH, COOH, $SO_3H$, $CH_3$, $NO_2$, CN, Cl, Br, CO—NOH-phenyl, or $OCH_3$.

B is preferably H or $C_{1-3}$-alkyl, said alkyl may contain hydroxy, ester or ether groups; preferably said alkyl may contain ester or ether groups; more preferably said alkyl may contain ether groups.

In an embodiment, A and B independently of each other are:

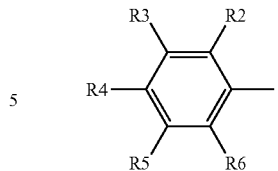

or B is H or $C_{1-3}$-alkyl, said alkyl may contain hydroxy, ester or ether groups (e.g. wherein the ether oxygen is directly attached to A-N(OH)C=O—, thus including N-hydroxy carbamic acid ester derivatives), and R2, R3, R4, R5 and R6 independently of each other are H, OH, $NH_2$, COOH, $SO_3H$, $C_{1-3}$-alkyl, acyl, $NO_2$, CN, Cl, Br, F, $CF_3$, NOH—CO-phenyl, CO—NOH-phenyl, COR12, OR7, NR8R9, COOR10, or NOH—CO—R11, wherein R7, R8 and R9 are $C_{1-3}$-alkyl or acyl, and R10, R11 and R12 are $C_{1-3}$-alkyl.

In another embodiment, A and B independently of each other are:

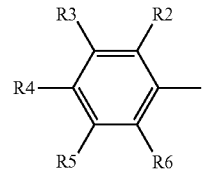

or B is H or $C_{1-3}$-alkyl, said alkyl may contain hydroxy or ether groups (e.g. wherein the ether oxygen is directly attached to A-N(OH)C=O—, thus including N-hydroxy carbamic acid ester derivatives), and R2, R3, R4, R5 and R6 independently of each other are H, OH, $NH_2$, COOH, $SO_3H$, $CH_3$, acyl, $NO_2$, CN, Cl, Br, F, $CF_3$, CO—NOH-phenyl, $COCH_3$, OR7, NR8R9, or $COOCH_3$, wherein R7, R8 and R9 are $CH_3$ or $COCH_3$.

In another embodiment, A and B independently of each other are:

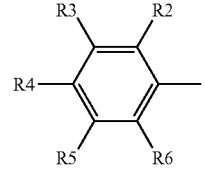

or B is H or $C_{1-3}$-alkyl, said alkyl may contain hydroxy or ether groups (e.g. wherein the ether oxygen is directly attached to A-N(OH)C=O—, thus including N-hydroxy carbamic acid ester derivatives), and R2, R3, R4, R5 and R6 independently of each other are H, OH, COOH, $SO_3H$, $CH_3$, acyl, $NO_2$, CN, Cl, Br, F, CO—NOH-phenyl, $OCH_3$, $COCH_3$, or $COOCH_3$.

In another embodiment, A and B independently of each other are:

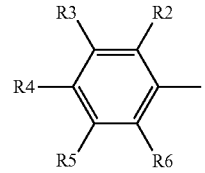

or B is $C_{1-3}$-alkyl, said alkyl may contain ether groups (e.g. wherein the ether oxygen is directly attached to A-N(OH)

C=O—, thus including N-hydroxy carbamic acid ester derivatives), and R2, R3, R4, R5 and R6 independently of each other are H, OH, COOH, SO$_3$H, CH$_3$, NO$_2$, CN, Cl, Br, CO—NOH-phenyl, or OCH$_3$.

The terms "C$_{1-n}$-alkyl" wherein n can be from 2 through 12, as used herein, represent a branched or straight alkyl group having from one to the specified number of carbon atoms. Typical C$_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl and the like.

The term "acyl" as used herein refers to a monovalent substituent comprising a C$_{1-6}$-alkyl group linked through a carbonyl group; such as e.g. acetyl, propionyl, butyryl, isobutyryl, pivaloyl, valeryl, and the like.

In an embodiment at least one of the substituents R2, R3, R4, R5 and R6 of A are H, preferably at least two of the substituents R2, R3, R4, R5 and R6 of A are H, more preferably at least three of the substituents R2, R3, R4, R5 and R6 of A are H, most preferably at least four of the substituents R2, R3, R4, R5 and R6 of A are H, in particular all of R2, R3, R4, R5 and R6 of A are H.

In another embodiment at least one of the substituents R2, R3, R4, R5 and R6 of B are H, preferably at least two of the substituents R2, R3, R4, R5 and R6 of B are H, more preferably at least three of the substituents R2, R3, R4, R5 and R6 of B are H, most preferably at least four of the substituents R2, R3, R4, R5 and R6 of B are H, in particular all of R2, R3, R4, R5 and R6 of B are H.

In particular embodiments according to the invention the enhancing agent is selected from the group consisting of
4-nitrobenzoic acid-N-hydroxyanilide;
4-methoxybenzoic acid-N-hydroxyanilide;
N,N'-dihydroxy-N,N'-diphenylterephthalamide;
decanoic acid-N-hydroxyanilide;
N-hydroxy-4-cyanoacetanilide;
N-hydroxy-4-acetylacetanilide;
N-hydroxy-4-hydroxyacetanilide;
N-hydroxy-3-(N'-hydroxyacetamide)acetanilide;
4-cyanobenzoic acid-N-hydroxyanilide;
N-hydroxy-4-nitroacetanilide;
N-hydroxyacetanilide;
N-hydroxy-N-phenyl-carbamic acid isopropyl ester;
N-hydroxy-N-phenyl-carbamic acid methyl ester;
N-hydroxy-N-phenyl-carbamic acid phenyl ester;
N-hydroxy-N-phenyl-carbamic acid ethyl ester; and
N-hydroxy-N-(4-cyanophenyl)-carbamic acid methyl ester.

Another group of preferred enhancing agents is phenolic compounds (alkylsyringates) of the general formula IV:

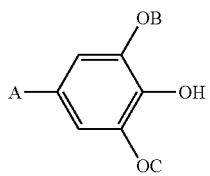

wherein the letter A in said formula denotes be a group such as -D, —CH=CH-D, —CH=CH—CH=CH-D, —CH=N-D, —N=N-D, or —N=CH-D, in which D is selected from the group consisting of —CO-E, —SO$_2$-E, —N—XY, and —N$^+$—XYZ, in which E may be —H, —OH, —R, or —OR, and X and Y and Z may be identical or different and selected from —H and —R; R being a C$_1$-C$_{16}$ alkyl, preferably a C$_1$-C$_8$ alkyl, which alkyl may be saturated or unsaturated, branched or unbranched and optionally substituted with a carboxy, sulpho or amino group; and B and C may be the same or different and selected from C$_m$H$_{2m+1}$, where m=1, 2, 3, 4 or 5.

In the above mentioned general formula IV, A may be placed meta to the hydroxy group instead of being placed in the para-position as shown.

In particular embodiments of the invention the enhancing agent is selected from the group having the general formula V:

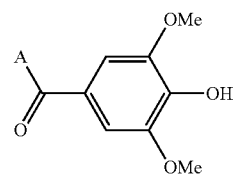

in which A is a group such as —H, —OH, —CH$_3$, —OCH$_3$, —O(CH$_2$)$_n$CH$_3$, where n=1, 2, 3, 4, 5, 6, 7 or 8.

Yet another group of preferred enhancing agents are the compounds as described in general formula VI:

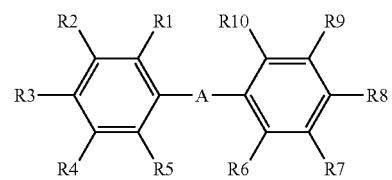

in which general formula A represents a single bond, or one of the following groups: (—CH$_2$—), (—CH=CH—), (—NR11-), (—CH=N—), (—N=N—), (—CH=N—N=CH—), or (>C=O);

and in which general formula the substituent groups R1-R11, which may be identical or different, independently represents any of the following radicals: hydrogen, halogen, hydroxy, formyl, acetyl, carboxy and esters and salts hereof, carbamoyl, sulfo and esters and salts hereof, sulfamoyl, methoxy, nitro, amino, phenyl, C$_{1-8}$-alkyl;

which carbamoyl, sulfamoyl, phenyl, and amino groups may furthermore be unsubstituted or substituted once or twice with a substituent group R12; and which C$_{1-8}$-alkyl group may be saturated or unsaturated, branched or unbranched, and may furthermore be unsubstituted or substituted with one or more substituent groups R12;

which substituent group R12 represents any of the following radicals: hydrogen, halogen, hydroxy, formyl, acetyl, carboxy and esters and salts hereof, carbamoyl, sulfo and esters and salts hereof, sulfamoyl, methoxy, nitro, amino, phenyl, or C$_{1-8}$-alkyl; which carbamoyl, sulfamoyl, and amino groups may furthermore be unsubstituted or substituted once or twice with hydroxy or methyl.

and in which general formula R5 and R6 may together form a group —B—, in which B represents a single bond, one of the following groups (—CH$_2$—), (—CH=CH—), (—CH=N—); or B represents sulfur, or oxygen.

In particular embodiments of the invention the enhancing agent is selected from the group having the general formula VII:

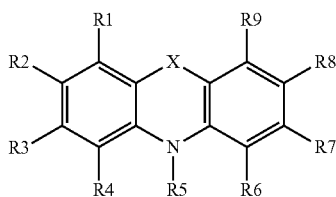

in which general formula X represents a single bond, oxygen, or sulphur;

and in which general formula the substituent groups R1-R9, which may be identical or different, independently represents any of the following radicals: hydrogen, halogen, hydroxy, formyl, acetyl, carboxy and esters and salts hereof, carbamoyl, sulfo and esters and salts hereof, sulfamoyl, methoxy, nitro, amino, phenyl, $C_{1-8}$-alkyl;

which carbamoyl, sulfamoyl, phenyl, and amino groups may furthermore be unsubstituted or substituted once or twice with a substituent group R10; and which $C_{1-8}$-alkyl group may be saturated or unsaturated, branched or unbranched, and may furthermore be unsubstituted or substituted with one or more substituent groups R10;

which substituent group R10 represents any of the following radicals: hydrogen, halogen, hydroxy, formyl, acetyl, carboxy and esters and salts hereof, carbamoyl, sulfo and esters and salts hereof, sulfamoyl, methoxy, nitro, amino, phenyl, or $C_{1-8}$-alkyl; which carbamoyl, sulfamoyl, and amino groups may furthermore be unsubstituted or substituted once or twice with hydroxy or methyl.

A further preferred enhancing agent according to the invention is 2,2',6,6'-tetramethyl-piperidine-N-oxyl (TEMPO):

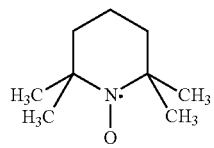

According to the invention, the enhancing agent may be present in a concentration in the range of from 0.01 mM to 1000 mM, preferably in the range of from 0.05 mM to 500 mM, more preferably in the range of from 0.1 mM to 100 mM, and most preferably in the range of from 0.1 mM to 50 mM.

Compositions

The present invention provides a composition comprising a polypeptide having laccase activity, a textile material and a dye or colorant, wherein the dye or colorant may be attached to the textile. In an embodiment, the composition also includes an enhancing agent.

The polypeptide having laccase activity, and optionally also the enhancing agent, may be formulated as a liquid (e.g. aqueous), a solid, a gel, a paste or a dry product formulation. The dry product formulation may subsequently be re-hydrated to form an active liquid or semi-liquid formulation usable in the method of the invention.

When the polypeptide having laccase activity and the enhancing agent are formulated as a dry formulation, the components may be mixed, arranged in discrete layers or packaged separately.

When other than dry form formulations are used and even in that case, it is preferred to use a two-part formulation system having the polypeptide having laccase activity separate from the enhancing agent.

The composition of the invention may further comprise auxiliary agents such as wetting agents, thickening agents, buffer(s) for pH control, stabilisers, perfume, colourants, fillers and the like.

Useful wetting agents are surfactants, i.e. non-ionic, anionic, amphoteric or zwitterionic surfactants. Surfactants are further described above.

When the composition of the invention includes water, the pH of such aqueous composition is in the range of from pH 2 to 12, preferably in the range of from pH 4 to 12, more preferably in the range of from pH 6 to 12, most preferably in the range of from pH 8 to 12, and in particular in the range of from pH 9 to 11.

Detergent Composition

The polypeptides having laccase activity of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptides having laccase activity of the invention and a surfactant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase (such as a laccase), and/or a peroxidase (such as a haloperoxidase).

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Lipases: Suitable lipases include those of bacterial or fungal origin. Chemically modified or protein engineered mutants are included. Examples of useful lipases include lipases from Humicola (synonym Thermomyces), e.g. from H. lanuginosa (T. lanuginosus) as described in EP 258 068 and EP 305 216 or from H. insolens as described in WO 96/13580, a Pseudomonas lipase, e.g. from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0.5-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a hydrogen peroxide source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, and the polypeptides having laccase activity of the invention, may be added in an amount corresponding to 0.01-100 mg of enzyme protein per liter of wash liquor, preferably 0.05-10 mg of enzyme protein per liter of wash liquor, more preferably 0.1-5 mg of enzyme protein per liter of wash liquor, and most preferably 0.1-1 mg of enzyme protein per liter of wash liquor.

The polypeptides having laccase activity of the invention may additionally be incorporated in the detergent formulations disclosed in WO 97/07202 which is hereby incorporated as reference.

Textile

In context of the invention the term "textile" includes fabrics, garments, and yarns.

Fabric can be constructed from fibers by weaving, knitting or non-woven operations. Weaving and knitting require yarn as the input whereas the non-woven fabric is the result of random bonding of fibers (paper can be thought of as nonwoven). In the present context, the term "fabric" is also intended to include fibers and other types of processed fabrics.

Woven fabric is constructed by weaving "filling" or weft yarns between wrap yarns stretched in the longitudinal direction on the loom. The wrap yarns must be sized before weaving in order to lubricate and protect them from abrasion at the high speed insertion of the filling yarns during weaving. The filling yarn can be woven through the warp yarns in a "over one—under the next" fashion (plain weave) or by "over one-under two" (twill) or any other myriad of permutations. Strength, texture and pattern are related not only to the type/quality of the yarn but also the type of weave. Generally, dresses, shirts, pants, sheeting's, towels, draperies, etc. are produced from woven fabric.

Knitting is forming a fabric by joining together interlocking loops of yarn. As opposed to weaving which is constructed from two types of yarn and has many "ends", knitted fabric is produced from a single continuous strand of yarn. As with weaving, there are many different ways to loop yarn together and the final fabric properties are dependent both upon the yarn and the type of knit. Underwear, sweaters, socks, sport shirts, sweat shirts, etc. are derived from knit fabrics.

Non-woven fabrics are sheets of fabric made by bonding and/or interlocking fibers and filaments by mechanical, thermal, chemical or solvent mediated processes. The resultant fabric can be in the form of web-like structures, laminates or films. Typical examples are disposable baby diapers, towels, wipes, surgical gowns, fibers for the "environmental friendly" fashion, filter media, bedding, roofing materials, backing for two-dimensional fabrics and many others.

According to the invention, the method of the invention may be applied to any fabric known in the art (woven, knitted, or non-woven). In particular the oxidation (bleaching) process may be applied to cellulose-containing or cellulosic fabrics, such as cotton, viscose, rayon, ramie, linen, lyocell (e.g. Tencel, produced by Courtaulds Fibers), or mixtures thereof, or mixtures of any of these fibers together with synthetic fibres (e.g., polyester, polyamid, nylon) or other natural fibers such as wool and silk, such as viscose/cotton blends, lyocell/cotton blends, viscose/wool blends, lyocell/wool blends, cotton/wool blends; flax (linen), ramie and other fabrics based on cellulose fibers, including all blends of cellulosic fibers with other fibers such as wool, polyamide, acrylic and polyester fibers, e.g., viscose/cotton/polyester blends, wool/cotton/polyester blends, flax/cotton blends etc. The term "wool," means any commercially useful animal hair product, for example, wool from sheep, camel, rabbit, goat, llama, and known as merino wool, Shetland wool, cashmere wool, alpaca wool, mohair, etc. and includes wool fiber and animal hair. The method of the invention can be used with wool or animal hair material in the form of top, fiber, yarn, or woven or knitted fabric. The enzymatic treatment can also be carried out on loose flock or on fibers made from wool or animal hair material. The treatment can be performed at many different stages of processing. The fabric to be bleached may be dyed or undyed. According to the invention textile may be desized, scoured and/or bleached in aqueous medium in the presence of a polypeptide having laccase activity of the invention.

Methods and Uses

The present invention provides methods for enzymatic oxidation of a substrate, comprising contacting the substrate at pH 9-12 with a polypeptide which has laccase activity and at least 60% identity with SEQ ID NO:2.

In an embodiment, the polypeptide retains at least 50% (preferably at least 60%, more preferably at least 70%, most preferably at least 80%) activity after exposure to pH 12 at 40 degrees Celsius for one hour.

The invention also provides methods for enzymatic oxidation of a substrate, comprising contacting the substrate at 50-100 degrees Celsius with a polypeptide which has laccase activity and at least 60% identity with SEQ ID NO:2.

In an embodiment, the polypeptide retains at least 50% (preferably at least 55%, more preferably at least 60%) residual activity after exposure to 90 degrees Celsius for one hour.

A substrate according to the invention may be a dye or colorant, a textile material, or lignin or a lignin containing material. Oxidation of the substrate occurs when it acts as an electron donor for the polypeptide having laccase activity or—when an enhancing agent is used—the enhancing agent. In a preferred embodiment, the method for oxidizing a substrate is a method for bleaching a substrate.

The following embodiments illustrate various uses of the invention.

In an embodiment, the method of the invention finds application for bleaching of a textile dye or colorant in solution or attached to textile. Bleaching includes changing the color of the dye/textile, such as whitening or fading the color of the dye/textile.

Colorants and dyes are broad classes of natural and synthetic compounds. The following description and examples of dyes/colorants are not intended to be in any way limiting to the scope of the invention as claimed.

Synthetic textile dyes bleachable by the method of the invention are typically azo compounds (with one or several azo, or diazenediyl, groups), as exemplified by Acid Red 151, Direct Blue 1, Direct Brown 44, and Orange II, or anthraquinone compounds, as exemplified by Acid Blue 45. Other structural motifs may occur together with these, as exemplified by Reactive Blue 19.

Another example of bleachable dyes is disperse dyes, which are characterized by being nonionic and have a very limited solubility in water. Disperse dyes include azo, nitroarylamine, and anthraquinone based dyes. Examples of disperse dyes include Disperse Red 60, Disperse Yellow 3, Disperse Blue 3, Disperse Blue 27, Disperse Blue 56, and Disperse Violet 1.

Some dyes furthermore carry groups capable of coupling to fabric surfaces (reactive dyes), and some dyes are complexed to metal ions. These modifications will often not influence the applicability of the present invention.

A different structure bleachable by the method of the invention is the indigo moiety, exemplified by the soluble dye indigo carmine.

Other dyes and colorants may be of natural origin or may be synthesized as identical to or resembling natural structures. Examples of categories of coloured substances extractable from vegetable sources are polyphenolic, anthocyanine and carotenoid compounds.

An embodiment of the present invention is provided by household and institutional laundering processes. In such washing and rinsing processes, dyes and colorants present on fabrics may leach into the washing or rinsing liquor and discoloration of the laundry may result. Bleaching of the coloured compounds in solution by the method of the invention may counteract this undesirable effect. Other systems for dye transfer inhibition are known in the art (e.g. WO 91/05839).

In another embodiment, dyes leached into process water during textile processing may be bleached by the method of the invention to prevent undesirable deposition. Other systems are known in the art (e.g. WO 92/18697).

In yet another embodiment, the method of the invention finds application in bleaching of pulp for paper production.

Accordingly, the invention provides a method for bleaching of lignin-containing material, in particular bleaching of pulp for paper production, which method comprises treatment of the lignin or lignin containing material with a polypeptide having laccase activity, and optionally an enhancing agent, as described in the present invention.

In yet another embodiment, the method of the invention finds application for lignin modification, e.g., in the manufacture of wood composites, e.g., wood fibre materials such as chipboards, fibre boards, or particle boards, or in the manufacture of laminated wood products, such as laminated beams and plywood.

In yet another embodiment, the method of the invention finds application in treatment of waste water, e.g., waste water from the chemical or pharmaceutical industry, from dye manufacturing, from dye-works, from the textile industry, or from pulp production (cf. e.g. U.S. Pat. No. 4,623,465, or JP-A-2-31887).

In a more specific embodiment, the invention provides a method for treatment of waste water from dye manufacturing, from dye-works, from textile industry, or from pulp manufacturing, the method comprising treatment of the waste water with a polypeptide having laccase activity according to the invention.

In the above mentioned processes and in other applications of the invention, an enhancing agent may be added at the beginning of the process or later, in one or several additions.

According to the invention the polypeptide having laccase activity may be present in concentrations of 0.001-100 mg enzyme protein per liter, preferably 0.005-50 mg enzyme protein per liter, more preferably 0.01-50 mg enzyme protein per liter, most preferably 0.05-10 mg enzyme protein per liter, and in particular 0.1-10 mg enzyme protein per liter.

Bleaching

According to the invention bleaching may be carried out using any known process conditions in the art. In an embodiment the bleaching may be carried out at a temperature in the range of from about 30° C. to about 100° C., more preferably from about 40° C. to about 90° C.

The pH range may be from about pH 5 to about pH 12, preferably from about pH 7 to about pH 12, more preferably from about pH 7 to about pH 11, even more preferably from about pH 8 to about pH 11, and most preferably from about pH 9 to about pH 11. The reaction time may preferably be in the range of from about 15 minutes to about 3 hours.

As mentioned above bleaching may result in a whitening of the textile. The value of whiteness index (WI) is measured using a MacBeth Color Eye equipped with Optiview 7000 software. The Whiteness index is calculated from the following equation:

$$WI = Y + 800(x_n - x) + 1700(y_n - y)$$

where Y, x and y are chromaticity coordinates of the sample, and $x_n$ and $y_n$ are those of illuminant using the standard illuminant D65 (imitating daylight).

The bleached materials may also be subject to additional processes. For example, for textile materials, the preparation may include the application of finishing techniques such as desizing and scouring, and other treatment processes, such as imparting antimicrobial properties (e.g., using quaternary ammonium salts), flame retardancy (e.g., by phosphorylation with phosphoric acid or urea), increasing absorbency (by coating or laminating with polyacrylic acid), providing an antistatic finish (e.g., using amphoteric surfactants (N-oleyl-N,N-dimethylglycine)), providing a soil release finish (e.g., using NaOH), providing an antisoiling finish (e.g., using a fluorochemical agent), and providing an antipilling finish (e.g., using NaOH, alcohol).

The method of the invention may be carried out in the presence of conventional fabric, fiber, or yarn finishing agents, including wetting agents, polymeric agents, dispersing agents, etc.

A conventional wetting agent may be used to improve the contact between the substrate and the enzyme used in the method. The wetting agent may be a nonionic surfactant, e.g. an ethoxylated fatty alcohol. A preferred wetting agent is an ethoxylated and propoxylated fatty acid ester such as Berol 087 (product of Akzo Nobel, Sweden).

Examples of suitable polymeris agents include proteins (e.g. bovine serum albumin, whey, casein or legume proteins), protein hydrolysates (e.g. whey, casein or soy protein hydrolysate), polypeptides, lignosulfonates, polysaccharides and derivatives thereof, polyethylene glycol, polypropylene glycol, polyvinyl pyrrolidone, ethylene diamine condensed with ethylene or propylene oxide, ethoxylated polyamines, or ethoxylated amine polymers.

The dispersing agent may preferably be selected from non-ionic, anionic, cationic, ampholytic or zwitterionic surfactants. More specifically, the dispersing agent may be selected from carboxymethylcellulose, hydroxypropylcellulose, alkyl aryl sulphonates, long-chain alcohol sulphates (primary and secondary alkyl sulphates), sulphonated olefins, sulphated monoglycerides, sulphated ethers, sulphosuccinates, sulphonated methyl ethers, alkane sulphonates, phosphate esters, alkyl isothionates, acylsarcosides, alkyltaurides, fluorosurfactants, fatty alcohol and alkylphenol condensates, fatty acid condensates, condensates of ethylene oxide with an amine, condensates of ethylene oxide with an amide, sucrose esters, sorbitan esters, alkyloamides, fatty amine oxides, ethoxylated monoamines, ethoxylated diamines, alcohol ethoxylate and mixtures thereof. A preferred dispersing agent is an alcohol ethoxylate such as Berol 08 (product of Akzo Nobel, Sweden).

The bleaching processing may be performed using any machinery known in the art.

The fabric may be further finished by one or more of the following treatments as are known in the art: dyeing, biopolishing, brightening, softening, and/or anti-wrinkling treatment(s).

Biofuel Cells—Biosensors

The integration of biomaterials with electronic elements, such as electrodes, yields hybrid bioelectronic systems that may function as biofuel cells, biosensors, bioelectronic circuitry, and their combinations. These self-contained wireless bioelectronic devices have possible use in medicine, high-tech industry, and biocomputing. The main difference between bioelectrodes in biofuel cells and biosensors is that the former requires as high as possible current densities, whereas for the latter, specificity and linearity are the important parameters. Biofuel cells are a subset of fuel cells that employ biocatalysts for conversion of chemical energy into electrical energy. A biological catalyst (e.g. glucose oxidase)

performs natural oxidation of fuel (e.g. β-D-glucose to D-glucono-1,5-lactone) at the anode, which results the release of electrons generating an electrical current. The electrons flow through an external circuit providing a resistance that serves as a load and electrons are then transferred to the cathode where another biocatalyst (e.g. blue multicopper oxidase) reduces oxygen to water.

The polypeptides having laccase activity of the invention may be used in both biofuel cells and in biosensors.

Biocatalysis

The integration of biocatalysis and organic synthesis is an important development in the fine chemical industry. The copper-dependent oxidase, laccase, provides the basis for the oxidation of alcohols. Laccase can oxidize an organic co-catalyst: 2,2,4,4-tetramethylpiperidinyloxy (TEMPO) to the corresponding oxoammonium ion. In a cascade reaction the thus formed oxoammonium ion can convert a wide range of alcohols to the corresponding ketones or aldehydes. The resulting hydroxylamine reverts back to TEMPO under the reaction conditions. Also, direct laccase-mediated oxidation of phenols generates reactive radical intermediates that undergo coupling reactions, leading to the formation of C—O and C—C dimers, oligomers and, eventually, polymers.

Accordingly, the polypeptides having laccase activity of the invention may be used in biocatalysis reactions.

Bioremediation and Waste Water Treatment

Laccase can be used in the detoxification, decolorization and odor removal of municipal, industrial and agricultural effluents. Laccase acts by oxidation and/or polymerization of common pollutants, such as phenols, aldehydes, aromatic amines and thiols. The laccase can act directly on the substrates, or via small molecule mediators. The oxidized products can then be removed from the effluents by filtration and/or sedimentation.

The polypeptides having laccase activity of the invention may be used in such bioremediation or waste water treatments.

Reference is made to the following publications:

S. Riva in TRENDS in Biotechnology Vol. 24 No. 5 May 2006 (Laccases: blue enzymes for green chemistry)

F. Davis in Biosensors and Bioelectronics 22 (2007) 1224-1235 (Biofuel cells—Recent advances and applications)

A. Wells in Biochemical Society Transactions (2006) Volume 34, part 2 304-308 (Green oxidations with laccase-mediator systems)

S. Minteer in Current Opinion in Biotechnology (2007), 18:228-234 (Enzyme-based biofuel cells)

A. M. Mayer and R. C. Staples in Phytochemistry (2002), 60: 551-565 (Laccase: new functions for an old enzyme)

The present invention is further described by the following examples that should not be construed as limiting the scope of the invention.

EXAMPLES

Plasmid pENI2516 was described in WO 2004/069872 Example 2.

*Aspergillus oryzae* strain ToC1512 was described in WO 2005/070962, Example 11.

```
primer SLAC_fwd_BamHI:
                                              (SEQ ID NO: 33)
AGGATTCACCATGGACAGGCGAGGCTTTAAC primer SLAC_rev_XhoI:
                                              (SEQ ID NO: 34)
ACTCGAGTCAGTGCTCGTGTTCGTGTGCGGC primer BamHI_trunc_SLAC_fwd:
                                              (SEQ ID NO: 35)
AGGATCCACCATGGCCCCCGCGGCCAAG primer pHUda_fwd:
                                              (SEQ ID NO: 36)
CCTTCACGGAGAAACCCCAGCG primer A_ory_sign_SLAC_rev:
                                              (SEQ ID NO: 37)
GATCCCCTTGGCCGCGGGGGCCCCGAGGGCCAGCTTCCCCAGC primer sign_SLAC_fwd:
                                              (SEQ ID NO: 38)
GCCCCCGCGGCCAAGGGGATC primer SgL_fwd_BamHI:
                                              (SEQ ID NO: 39)
AGGATCCACCATGGACCGAAGGACCTTCAGCCG primer SgL_rev_XhoI:
                                              (SEQ ID NO: 40)
ACTCGAGTCAGTGCTGGTGCTCCGC
```

Example 1

Cloning of Recombinant *Streptomyces coelicolor* Laccase

The laccase gene was obtained from the M145 derivative of *Streptomyces coelicolor* A3(2). The strain (NCTC ref no. 13224) was obtained from the National Collection of Type Cultures in London. Genomic DNA was prepared using FastDNA® SPIN Kit for Soil from Qbiogene Inc. The genomic DNA was used as template in a PCR reaction. The Phusion DNA polymerase from Finnzymes (Espoo, Finland) was used for the PCR in combination with the GC buffer due to the GC rich nature of the template DNA.

PCR mixture:
10 μL Phusion buffer GC
5 μL dNTPs (2.5 mM)
0.5 μL forward primer SLAC fwd_BamHI (100 μM)
0.5 μL reverse primer SLAC_rev_XhoI (100 μM)
1 μL gDNA (10× diluted)
0.5 μL Phusion polymerase
H$_2$O to 50 μL
PCR cycle:
Step 1: 30" at 98° C.
Step 2: 10" at 98° C.; 20" at 60° C.; 45" at 72° C.; repeat 35 times
Step 3: 10' at 72° C.
Step 4: Hold at 4° C.

The PCR reaction resulted in a single band (visible on an agarose gel) of approximately 1100 basepair size comprising the laccase coding sequence including its native signal peptide coding sequence. This coding sequence is shown in SEQ ID NO:1. The band was extracted from the gel by Qiagen's QIAquick Gel Extraction Kit. The recovered DNA was subsequently subjected to restriction at 37° C. for 3 hours:
15 μL DNA
2 μL NEB buffer 2
0.5 μL XhoI
0.5 μL BamHI The cut DNA was gel-cleaned and ligated into pENI2516 as a BamHI-XhoI fragment to create plasmid ScL-wt. The resulting plasmid was initially transformed into *E. coli* strain DH10B and the insert was sequenced to confirm its nucleotide sequence. The plasmid was subsequently transformed into *Aspergillus oryzae* strain ToC1512 for expression.

Fermentation

The transformed strain of *A. oryzae* was grown for expression of laccase enzyme. Typically, a 100 mL of YP media was inoculated with spores from a stock in 50% glycerol stored at −80° C. The starter culture was grown in a baffled 250 mL flask for 3-4 days at 37° C. and 180 rpm. Twenty mL of this culture was then used to inoculate 500 mL MY51 medium added 2% maltose and 500 µM $CuSO_4$ in a 2 L flask with baffles. The flask was placed in an orbital shaker at 180 rpm and grown for one week at 37° C. before being harvested. The enzymatic activity in the broth was monitored daily using the described assay. Only the construct with the TAT-leader sequence produced an active enzyme of the correct size, which was determined by assay and SDS-PAGE analysis of the crude broth.

Purification

The fermentation broth was filtered using Mira cloth to remove fungal hyphae. This filtrate was subsequently sterile filtered using a Corning 0.45 µm filter with pre-filter. The resulting filtrate was made 1.2 M in ammonium sulphate and loaded onto a XK16 column with 15 mL Source 15Phe media pre-equilibrated with 1.2 M ammonium sulphate. The column was then washed with 1.2 M ammonium sulphate at 10 mL/min until a stable baseline was reached. The bound protein was eluted with 10 mM Tris-HCl (pH 8.0). Five mL fractions were collected. The fractions of a clear blue colour, indicative of laccase enzyme, were pooled. The pooled fractions were washed using an Amicon cell with a 10 kDa cut-off filter to remove ammonium sulphate and to exchange the buffer to 50 mM borate buffer (pH 9.0). The washed protein solution was then loaded onto a XK16 column with 15 mL Source 15Q media pre-equilibrated with 50 mM borate buffer (pH 9.0). The column was washed with the same buffer until a stable baseline was reached. The bound protein was eluted with a linear gradient from 0 to 0.5 M NaCl in 50 mM borate buffer (pH 9.0) over 20 column volumes. Fractions of 10 mL were collected. The fractions containing pure laccase, as estimated by SDS-PAGE, spectroscopy and activity assay, were pooled and concentrated. The concentrated solution of enzyme was stored at −20° C. until use. All purification steps were carried out at room temperature.

Assay

The enzymatic activity was determined spectrophotometrically by oxidation of syringaldazine at 30° C.: 10 µL enzyme (0.8 mg/mL) was added to a 1 cm quartz cuvette containing 1 mL 25 mM Tris-malate buffer (pH 7.5) and 75 µL 0.28 mM syringaldazine. The change in absorbance at 530 nm was monitored for 90 seconds. The slope of the progress curve was used to calculate the initial rate of the reaction.

Example 2

*Streptomyces coelicolor* Laccase is Only Active as a Trimer

It was demonstrated that the *Streptomyces coelicolor* Laccase is active only as a trimer by analysis of the individual species (monomer, dimer, trimer) after SDS-PAGE.

Briefly, 10 µg purified wild-type enzyme was added to:
1) standard SDS-loading buffer without reducing agent, and no boiling before being loaded on the gel;
2) standard SDS-loading buffer without reducing agent, but boiled for 3 minutes before being loaded on the gel; and
3) standard SDS-loading buffer with reducing agent, and boiled for 3 minutes before being loaded on the gel.

Duplicate samples were loaded on the gel. One set of samples were stained by standard Coomassie Blue to visualise the protein bands. The other set was added an overlay of 1% agarose, 1 mM 2,6-dimethoxyphenol (2,6-DMP) and 50 mM Tris-HCl, pH 8.0, in order to visualise laccase activity.

The results showed that only the trimer was capable of oxidizing 2,6-DMP, whereas the dimer and monomer had no such activity.

Example 3

Site-Directed Mutagenesis of *Streptomyces coelicolor* Laccase

All variants were constructed based on the *Streptomyces coelicolor* laccase expression vector ScL-wt, described in Example 1. The mutation primers used in the constructions are summarized in Table 1.

TABLE 1

| Primer | SEQ ID NO: | Sequence |
|---|---|---|
| 1 | 9 | (forward) 5'-AGGATCCACCATGG ACAGGCGAGGCTTTAAC-3' |
| 2 | 10 | (reverse) 5'-ACTCGAGTCAGT GCTCGTGTTCGTGTGCGGC-3' |
| 3 | 11 | 5'-ACCGGCCCCGACGACG CCTCCCGGGTCATCGAC-3' |
| 4 | 12 | (forward) 5'-GGCCCCGACGACCC GAACCGGGTCATCGACAAC-3' |
| 5 | 13 | (reverse) 5'-GTTGTCGATGACCC GGTTCGGGTCGTCGGGGCC-3' |
| 6 | 14 | 5'-CAGAGCCACTCCGA CGCCGGCATGGTGG-3' |
| 7 | 15 | 5'-GATCACGCACGGGGAGCAT TACCACACCTTCCACATGC-3' |
| 8 | 16 | 5'-ATCGTCTTCAACGACA CCATCAACAACCGCAAG-3' |
| 9 | 17 | 5'-CTTCAACGACGCGACCATCAAC-3' |
| 10 | 18 | 5'-CCACTGCCACGTCCAGG AACACTCCGACATGGGC-3' |
| 11 | 19 | 5'-GATCACGCACGGGTCGT ACTACCACACCTTCCAC-3' |
| 12 | 20 | 5'-CCACTGCCACGTCCAGC AGCACTCCGACATGGGC-3' |
| 13 | 21 | 5'-CCACTGCCACGTCCAGA AGCACTCCGACATGGGC-3' |
| 14 | 22 | 5'-CAGAGCCACTCCGA CTGGGGCATGGTGG-3' |
| 15 | 23 | 5'-GACAACCGGACCGGCG CCCTCACCGGCCCCGAC-3' |
| 16 | 24 | 5'-GACAACCGGACCGGCC TCCTCACCGGCCCCGAC-3' |
| 17 | 25 | 5'-GGCGCCGGGGCGTGGC TCTACCACTGCCACGTC-3' |

TABLE 1-continued

| Primer | SEQ ID NO: | Sequence |
|---|---|---|
| 18 | 26 | 5'-CACGTCGTCGGCACCG CCCACGGCACCGGAGGC-3' |
| 19 | 27 | 5'-GATCGAGGTCAACGAGT CCGACACGCTGCATATC-3' |
| 20 | 28 | 5'-GATCACGCACGGGTCGTGG TACCACACCTTCCACATGC-3' |

The 1046 bp gene fragments were constructed by standard overlap extension (SOE) PCR and purified with a Qiagen's QIAquick PCR purification kit. All PCR reactions were performed in 50 µL scale, using Pfu polymerase and following standard protocols. The PCR products were digested with BamHI plus XhoI restriction enzymes and purified by agarose gel electrophoresis. The digested fragments were inserted into the plasmid pENI2516 (described in WO 2004/069872, Example 2), using T4 DNA ligase. The acceptor plasmid pENI2516 was previously prepared by restriction digest with BamHI plus XhoI restriction enzymes and purified by agarose gel electrophoresis. The resulting ligated plasmids were transformed into calcium competent TOP10 *Escherichia coli* cells, isolated and the inserts were verified by sequencing. The plasmids were subsequently transformed into *Aspergillus oryzae* strain ToC1512 for expression. A summary of the plasmids and mutations is shown in Table 2.

TABLE 2

| Variant | Plasmid | Template | Primer(s) used | Mutation |
|---|---|---|---|---|
| A | ScL-1 | ScL-wt | 1, 2, 3 | P224A |
| B | ScL-2 | ScL-wt | 1, 2, 4, 5 | S225N |
| C | ScL-3 | ScL-wt | 1, 2, 6 | M266A |
| D | ScL-4 | ScL-wt | 1, 2, 7 | Y199W |
| E | ScL-5 | ScL-wt | 1, 2, 8 | M168G |
| F | ScL-6 | ScL-wt | 1, 2, 9 | M168A |
| G | ScL-7 | ScL-6 | 1, 2, 10, 11 | M168A + E198S + S262E |
| H | ScL-8 | ScL-7 | 1, 2, 12 | M168A + E198S + S262Q |
| J | ScL-9 | ScL-7 | 1, 2, 13 | M168A + E198S + S262K |
| K | ScL-10 | ScL-5 | 1, 2, 14 | M168G + M266W |
| L | ScL-11 | ScL-5 | 1, 2, 6 | M168G + M266A |
| M | ScL-12 | ScL-wt | 1, 2, 15 | I217A |
| N | ScL-13 | ScL-wt | 1, 2, 16 | I217L |
| O | ScL-14 | ScL-wt | 1, 2, 17 | M255L |
| P | ScL-15 | ScL-wt | 1, 2, 18 | E133A |
| Q | ScL-16 | ScL-wt | 1, 2, 19 | G54S |
| R | ScL-17 | ScL-wt | 1, 2, 14 | M266W |
| S | ScL-18 | ScL-7 | 1, 2, 20 | M168A + E198S + S262E + Y199W |
| T | ScL-19 | ScL-2 | 1, 2, 8 | M168G + S225N |
| U | ScL-20 | ScL-10 | 1, 2, 7 | M168G + Y199W + M266W |

Example 4

Characterization of the *Streptomyces coelicolor* Laccase Variants

The enzymatic activity of the produced variants was analyzed (and compared to wild-type) using three assays:
(1) Syringaldazine oxidation;
(2) Ferrocyanide oxidation;
(3) Dimethoxyphenol oxidation; and
(4) Indigo carmine bleaching.

All assays were performed in Nunc 96-well plates and the change in absorbance measured in a SpectraMax 384 plus UV-Vis spectrophotometer plate-reader from Molecular Devices. All variants were used as 5 µM stock solutions.

In the Syringaldazine oxidation assay (1), 20 µL of enzyme solution were reacted with 180 mL of a 20 µM solution of syringaldazine in 25 mM Tris/malate buffer pH 7.5. The increase in absorbance at 530 nm was monitored for 90 seconds and the slope of the progress curve was used to calculate the initial rate of the reaction.

In the Ferrocyanide oxidation assay (2), a reaction mixture comprising 20 µL of enzyme solution, 100 µL of 100 mM Briton&Robinson buffer (pH 5.0) and 60 µL of water was prepared in each well. The reaction was initiated with addition of 20 µL of 50 mM potassium ferrocyanide solution, and the increase in absorbance at 405 nm was monitored for 90 seconds. The slope of the progress curve was used to calculate the initial rate of the reaction.

In the Dimethoxyphenol oxidation assay (3), a reaction mixture comprising 20 µL of enzyme solution, 100 µL of 100 mM Briton&Robinson buffer (pH 8.0) and 60 µL of water was prepared in each well. The reaction was initiated with addition of 20 µL of 75 mM 2,6-dimethoxyphenol solution, and the increase in absorbance at 468 nm was monitored for 90 seconds. The slope of the progress curve was used to calculate the initial rate of the reaction.

In the Indigo carmine bleaching assay (4), a reaction mixture comprising 20 µL of enzyme solution, 100 µL of 100 mM Briton&Robinson buffer (pH 5.0, 7.0 or 9.0) and 20 µL of 10 mM mediator solution (methylsyringate, 10-phenothiazine-propionic acid (PPT) or 2,2',6,6'-tetramethyl-piperidine-N-oxyl (TEMPO)) or water was prepared in each well. The reaction was initiated with addition of 100 µL of 0.2 mg/mL indigo carmine solution, and the decrease in absorbance at 610 nm was monitored for 90 seconds. The slope of the progress curve was used to calculate the initial rate of the reaction.

The results from the activity assays with Syringaldazine (1), Ferrocyanide (2) and Dimethoxyphenol (3) are shown in Table 3.

TABLE 3

Activities of the variants are relative to the activity of the wild-type laccase.

| | Relative activity | | |
|---|---|---|---|
| Variant | Syringaldazine | Ferrocyanide | Dimethoxyphenol |
| wildtype | 1.0 | 1.0 | 1.0 |
| A | 5.3 | 2.9 | 3.1 |
| B | 3.2 | 2.0 | 1.6 |
| C | 5.4 | 2.7 | 3.0 |
| D | 4.0 | 1.2 | 1.6 |
| E | 8.9 | 2.0 | 7.1 |
| F | 5.4 | 1.3 | — |
| G | 7.3 | 1.0 | 2.6 |
| H | 5.5 | 0.7 | 2.7 |
| J | 8.9 | 1.2 | 5.4 |
| K | 3.0 | 1.7 | 3.4 |
| L | 4.6 | 2.5 | 7.4 |
| M | 1.5 | 1.5 | 1.5 |
| N | 1.4 | 1.5 | 1.5 |
| O | 2.0 | 2.8 | 1.2 |
| P | 1.3 | 1.2 | 0.7 |
| Q | 1.5 | 1.7 | 1.5 |
| R | 2.8 | 2.5 | 3.4 |
| S | 5.1 | 1.5 | 3.9 |
| T | 3.7 | 2.6 | 6.7 |
| U | 1.4 | 0.7 | 1.8 |

The results from the activity assays with Indigo carmine (4) are shown in Table 4.

TABLE 4

Activities of the variants are relative to the activity of the wild-type laccase.

| | Relative activity | | | | | | | | | | | |
|---|---|---|---|---|---|---|---|---|---|---|---|---|
| | Without mediator | | | Methylsyringate | | | PPT | | | TEMPO | | |
| Variant | pH 5 | pH 7 | pH 9 | pH 5 | pH 7 | pH 9 | pH 5 | pH 7 | pH 9 | pH 5 | pH 7 | pH 9 |
| wildtype | bkg | bkg | bkg | bkg | 1.0 | 1.0 | 1.0 | 1.0 | 1.0 | bkg | bkg | bkg |
| A | nd | nd | nd | nd | 1.7 | 4.5 | 4.2 | 4.4 | 4.0 | 11.6 | 10.6 | 9.0 |
| B | nd | nd | nd | 5.2 | 3.4 | 2.5 | 2.5 | 3.4 | 2.1 | 17.1 | 4.3 | 6.6 |
| C | nd | nd | nd | 6.6 | 4.1 | 3.5 | 3.4 | 5.0 | 3.2 | 18.4 | 6.4 | 3.4 |
| D | nd | nd | nd | 7.4 | 3.9 | 4.0 | 2.6 | 4.3 | 3.3 | 19.2 | 6.4 | 4.8 |
| E | nd | nd | nd | 13.1 | 8.3 | 5.5 | 4.1 | 4.3 | 3.2 | 46.8 | 23.1 | 14.7 |
| F | nd | nd | nd | 4.0 | 4.1 | 2.9 | 2.1 | 3.2 | 2.4 | 23.4 | 12.0 | 5.8 |
| G | nd | nd | nd | 13.4 | 5.1 | 3.4 | 3.8 | 4.0 | 2.4 | 45.2 | 14.2 | 10.6 |
| H | nd | nd | nd | 8.2 | 3.8 | 1.8 | 1.8 | 2.0 | 1.0 | 14.4 | 6.0 | 3.8 |
| J | nd | nd | 4.0 | 10.4 | 7.2 | 2.9 | 3.1 | 3.6 | 2.1 | 28.6 | 16.2 | 9.8 |
| K | nd | nd | nd | 4.7 | 2.6 | 1.6 | 1.7 | 2.2 | 1.5 | 21.0 | 12.4 | 7.9 |
| L | nd | nd | nd | 5.9 | 6.2 | 2.8 | 2.3 | 4.1 | 2.2 | 42.2 | 35.2 | 17.4 |
| M | nd | nd | nd | nd | 1.4 | 1.1 | 1.5 | 2.0 | 1.2 | 4.7 | 4.8 | 3.0 |
| N | nd | nd | nd | nd | 1.3 | 1.3 | 1.5 | 1.9 | 1.1 | 5.1 | 5.9 | 3.1 |
| O | nd | nd | nd | nd | 1.2 | 1.0 | 1.4 | 1.7 | 1.0 | 6.2 | 3.1 | nd |
| P | nd | nd | nd | nd | 1.4 | 0.8 | 1.3 | 1.5 | 0.8 | 3.7 | 2.0 | nd |
| Q | nd | nd | nd | nd | 1.4 | 1.0 | 1.7 | 2.1 | 1.2 | 3.0 | 3.3 | 3.9 |
| R | nd | nd | nd | 5.8 | 3.7 | 2.8 | 4.1 | 6.6 | 3.0 | 14.8 | 7.1 | 4.2 |
| S | nd | nd | nd | 12.1 | 7.3 | 2.9 | 3.7 | 4.2 | 1.8 | 7.7 | 6.3 | 6.2 |
| T | nd | nd | nd | 7.6 | 6.9 | 3.8 | 4.5 | 6.3 | 2.6 | 26.3 | 20.6 | 10.6 |
| U | nd | nd | nd | nd | 2.1 | 1.4 | 1.8 | 2.6 | 1.5 | 6.1 | 6.7 | 6.0 |

"bkg" means that no enzymatic activity was detected for the wildtype enzyme, under the specific reaction conditions. The activities of the variants are, therefore, relative to the background reaction (reaction in the absence of enzyme); and "nd" means that no enzymatic activity was detected for the variant, under the specific reaction conditions.

Example 5

Cloning of Recombinant *Streptomyces griseus* Laccase

The laccase gene was obtained from *Streptomyces griseus* subsp. *griseus*. The strain (NBRC 13350) was obtained from the NITE Biological Resource Center (NBRC) in Chiba, Japan. Genomic DNA was prepared using FastDNA® SPIN Kit for Soil from Qbiogene Inc. The genomic DNA was used as template in a PCR reaction. The Phusion DNA polymerase from Finnzymes (Espoo, Finland) was used for the PCR in combination with the HF.

PCR mixture:
10 μL Phusion buffer HF
4 μL dNTPs (2.5 mM)
0.5 μL forward primer SgL_fwd_BamHI (100 μM)
0.5 μL reverse primer SgL_rev_XhoI (100 μM)
1 μL gDNA (10× diluted)
0.5 μL Phusion polymerase
H$_2$O to 50 μL PCR cycle:
Step 1: 30" at 98° C.
Step 2: 5" at 98° C.; 30" at 65° C.; 30" at 72° C.; repeat 25 times
Step 3: 7' at 72° C.
Step 4: Hold at 4° C.

The PCR reaction resulted in a single band (visible on an agarose gel) of approximately 1100 basepair size comprising the laccase coding sequence including its native signal peptide coding sequence. This coding sequence is shown in SEQ ID NO 3. The band was extracted from the gel by Qiagen's QIAquick Gel Extraction Kit. The recovered DNA was subsequently subjected to restriction at 37° C. for 3.5 hours:

20 μL DNA
4 μL NEB buffer 2
4 μL (10× dil) BSA
2 μL XhoI
2 μL BamHI
H$_2$O to 40 μL The cut DNA was gel-cleaned and ligated into pENI2516 as a BamHI-XhoI fragment to create pSgL-wt. The resulting plasmid was initially transformed into *E. coli* strain DH10B and the insert was sequenced to confirm its nucleotide sequence. The plasmid was subsequently transformed into *Aspergillus oryzae* strain ToC1512 for expression.

Fermentation

The transformed strain of *A. oryzae* was grown for expression of laccase enzyme. Typically, a 100 mL of YP media was inoculated with spores from a stock in 50% glycerol stored at −80° C. The starter culture was grown in a baffled 250 mL flask for 3-4 days at 37° C. and 180 rpm. Twenty mL of this culture was then used to inoculate 500 mL MY50 medium added 2% maltose and 500 μM CuSO$_4$ in a 2 L flask with baffles. The flask was placed in an orbital shaker at 180 rpm and grown for one week at 37° C. before being harvested. The enzymatic activity in the broth was monitored daily using the described assay. Only the construct with the TAT-leader sequence produced an active enzyme of the correct size, which was determined by assay and SDS-PAGE analysis of the crude broth.

Purification

The fermentation broth was filtered using Mira cloth to remove fungal hyphae. This filtrate was subsequently sterile filtered using a Corning 0.45 μm filter with pre-filter. The resulting filtrate was made 1.2 M in ammonium sulphate and loaded onto a XK16 column with 15 mL Toyopearl Phenyl media pre-equilibrated with 1.2 M ammonium sulphate. The column was then washed with 1.2 M ammonium sulphate at 10 mL/min until a stable baseline was reached. The bound protein was eluted with 10 mM Tris-HCl (pH 7.5). Ten mL fractions were collected. The fractions of a clear blue colour, indicative of laccase enzyme, were pooled. The pooled fractions were washed using an Amicon cell with a 10 kDa cut-off filter to remove ammonium sulphate and to exchange the buffer to 50 mM Tris-HCl (pH 7.5). The washed protein solution was then loaded onto a XK16 column with 15 mL Source S media pre-equilibrated with 50 mM Tris-HCl (pH 7.5). The column was washed with the same buffer until a stable baseline was reached. The bound protein was eluted with a linear gradient from 0 to 0.5 M NaCl in 50 mM Tris-HCl (pH 7.5) over 20 column volumes. Fractions of 10 mL were collected. The fractions containing pure laccase, as estimated by SDS-PAGE, spectroscopy and activity assay, were pooled and concentrated. The concentrated solution of enzyme was stored at −20° C. until use. All purification steps were carried out at room temperature.

Assay

The enzymatic activity was determined spectrophotometrically by oxidation of syringaldazine at 30° C.: Ten μL enzyme (0.8 mg/mL) was added to a 1 cm quartz cuvette containing 1 mL 25 mM Tris-malate buffer (pH 7.5) and 75 μL 0.28 mM syringaldazine. The change in absorbance at 530 nm was monitored for 90 seconds. The slope of the progress curve was used to calculate the initial rate of the reaction.

Example 6

Site-Directed Mutagenesis of Streptomyces griseus Laccase

All variants were constructed based on the Streptomyces griseus laccase expression vector SgL-wt, described in Example 5. The mutation primers used in the constructions are summarized in Table 5.

TABLE 5

| Primer | SEQ ID NO: | Sequence |
|---|---|---|
| 21 | 29 | (forward) 5'-AGGATCCACCATGG ACCGAAGGACCTTCAGCCG-3' |
| 22 | 30 | (reverse) 5'-ACTCGAGTCAGTGC TGGTGCTCCGC-3' |
| 23 | 31 | 5'-CATGATCACGCACGGTAGTTTCTA CCACACCTTC-3' |
| 24 | 32 | 5'-CACTGTCACGTGCAGACGCACTCC GACATGGGG-3' |

The 1064 bp gene fragments were constructed by standard overlap extension (SOE) PCR and purified with a Qiagen's QIAquick PCR purification kit. All PCR reactions were performed in 50 μL scale, using Phusion polymerase and following standard protocols. The PCR products were digested with BamHI plus XhoI restriction enzymes and purified by agarose gel electrophoresis. The digested fragments were inserted into the plasmid pENI2516, using T4 DNA ligase. The acceptor plasmid pENI2516 was previously prepared by restriction digest with BamHI plus XhoI restriction enzymes and purified by agarose gel electrophoresis. The resulting ligated plasmids were transformed into calcium competent TOP10 Escherichia coli cells, isolated and the inserts were verified by sequencing. The plasmids were subsequently transformed into Aspergillus oryzae strain ToC1512 for expression. A summary of the plasmid details is provided in Table 6.

TABLE 6

| Variant | Plasmid | Template | Primers | Mutation |
|---|---|---|---|---|
| V | SgL-1 | SgL-wt | 21, 22, 23, 24 | E228S + S292T |

Example 7

Characterization of the Streptomyces griseus Laccase Variants

The enzymatic activity of the produced variants was analyzed (and compared to wild-type) using three assays:

(1) Syringaldazine oxidation;

(2) Ferrocyanide oxidation;

(3) Dimethoxyphenol oxidation; and (4) Indigo carmine bleaching.

All assays were performed in Nunc 96-well plates and the change in absorbance measured in a SpectraMax 384 plus UV-Vis spectrophotometer plate-reader from Molecular Devices. All variants were used as 5 μM stock solutions.

In the Syringaldazine oxidation assay (1), 20 μL of enzyme solution were reacted with 180 mL of a 20 μM solution of syringaldazine in 25 mM Tris/malate buffer pH 7.5. The increase in absorbance at 530 nm was monitored for 90 seconds and the slope of the progress curve was used to calculate the initial rate of the reaction.

In the Ferrocyanide oxidation assay (2), a reaction mixture comprising 20 μL of enzyme solution, 100 μL of 100 mM Briton&Robinson buffer (pH 5.0 and pH 7.0) and 60 μL of water was prepared in each well. The reaction was initiated with addition of 20 μL of 50 mM potassium ferrocyanide solution, and the increase in absorbance at 405 nm was monitored for 90 seconds. The slope of the progress curve was used to calculate the initial rate of the reaction.

In the Dimethoxyphenol oxidation assay (3), a reaction mixture comprising 20 μL of enzyme solution, 100 μL of 100 mM Briton&Robinson buffer (pH 5.0, pH 7.0 and pH 9.0) and 60 μL of water was prepared in each well. The reaction was initiated with addition of 20 μL of 75 mM 2,6-dimethoxyphenol solution, and the increase in absorbance at 468 nm was monitored for 90 seconds. The slope of the progress curve was used to calculate the initial rate of the reaction.

In the Indigo carmine bleaching assay (4), a reaction mixture comprising 20 μL of enzyme solution, 100 μL of 100 mM Briton&Robinson buffer (pH 5.0, 7.0 or 9.0) and 20 μL of 10 mM mediator solution (methylsyringate or potassium ferrocyanide) or water was prepared in each well. The reaction was initiated with addition of 100 μL of 0.2 mg/mL indigo carmine solution, and the decrease in absorbance at 610 nm was monitored for 90 seconds. The slope of the progress curve was used to calculate the initial rate of the reaction.

The results from the activity assays with Syringaldazine (1), Ferrocyanide (2) and Dimethoxyphenol (3) are shown in Table 7.

TABLE 7

Activity of the variant is relative to the activity of the wild-type laccase.

| | Relative activity | | | | | |
|---|---|---|---|---|---|---|
| | Syringaldazine | Ferrocyanide | | Dimethoxyphenol | | |
| Variant | pH 7.5 | pH 5.0 | pH 7.0 | pH 5.0 | pH 7.0 | pH 9.0 |
| wild-type | 1.0 | 1.0 | 1.0 | 1.0 | 1.0 | 1.0 |
| V | 9.5 | 0.9 | 10.7 | 1.5 | 7.5 | 0.2 |

The results from the activity assays with Indigo carmine (4) are shown in Table 8.

TABLE 8

Activity of the variant is relative to the activity of the wild-type laccase.

| | Relative activity | | | | | | | | |
|---|---|---|---|---|---|---|---|---|---|
| | Without mediator | | | Methylsyringate | | | Ferrocyanide | | |
| Variant | pH 5 | pH 7 | pH 9 | pH 5 | pH 7 | pH 9 | pH 5 | pH 7 | pH 9 |
| wild-type | bkg | bkg | bkg | bkg | 1.0 | 1.0 | 1.0 | bkg | 1.0 |
| V | nd | nd | 11.8 | 4.1 | 2.1 | 0.6 | 1.8 | 262 | 5.3 |

"bkg" means that no enzymatic activity was detected for the wildtype enzyme, under the specific reaction conditions. The activities of the variants are, therefore, relative to the background reaction (reaction in the absence of enzyme); and "nd" means that no enzymatic activity was detected for the variant, under the specific reaction conditions.

---

The invention claimed is:

1. An isolated variant laccase comprising an amino acid sequence having at least 95% sequence identity to the mature polypeptide of SEQ ID NO:2, wherein the variant has laccase activity, and wherein the variant has a substitution at a position corresponding to position M168 of SEQ ID NO: 2.

2. The isolated variant of claim 1, wherein the amino acid sequence has at least 97% sequence identity to the mature polypeptide of SEQ ID NO:2.

3. The isolated variant of claim 1, wherein the amino acid sequence has at least 97% sequence identity to the mature polypeptide of SEQ ID NO:2 or to amino acids 9 to 293 of SEQ ID NO: 2.

4. An isolated variant laccase comprising a substitution at a position corresponding to position M168 of SEQ ID NO: 2, wherein the variant has laccase activity and is a polypeptide comprising an amino acid sequence having at least 95% sequence identity to the mature polypeptide of SEQ ID NO:2 or to amino acids 9 to 293 of SEQ ID NO: 2.

5. A variant laccase comprising a substitution at a position corresponding to position M168 of SEQ ID NO: 2, wherein the variant has laccase activity and is a polypeptide comprising an amino acid sequence having at least 95% sequence identity to the mature polypeptide of SEQ ID NO:2 or to amino acids 9 to 293 of SEQ ID NO: 2.

6. The variant of claim 5, wherein the variant is a polypeptide comprising an amino acid sequence having at least 97% sequence identity to amino acids 9 to 293 of SEQ ID NO: 2.

7. The variant of claim 5, wherein the variant is a polypeptide comprising an amino acid sequence having at least 97% sequence identity to the mature polypeptide of SEQ ID NO:2.

8. The variant of claim 5, wherein the variant consists of a substitution at a position corresponding to position M168 of the mature polypeptide of SEQ ID NO: 2.

9. The variant of claim 5, wherein the variant comprises the substitution M168A.

10. The variant of claim 5, wherein the variant comprises the substitution M168G.

11. The variant of claim 5, wherein the variant comprises substitutions selected from the group consisting of M168G+M266W; M168G+M266A; M168A+E198S+S262E; M168A+E198S+S262Q; M168A+E198S+S262K; M168A+E198S+S262E+Y199W; M168G+S225N; and M168G+Y199W+M266W.

12. The variant of claim 5, wherein the variant has one or more improved properties compared to the parent laccase, wherein the improved properties are selected from the group consisting of thermal activity, thermostability, pH activity, and oxidative stability.

13. A detergent composition comprising a surfactant and the variant of claim 5.

14. A composition comprising the variant of claim 5 and an enhancing agent.

15. A method for enzymatic oxidation of a substrate, comprising contacting the substrate with a variant of claim 5.

16. The method of claim 15, wherein the substrate is contacted with the polypeptide at pH 8-12.

17. The method of claim 15, wherein the substrate is a dye or colorant, such as indigo.

18. The method of claim 15, wherein the substrate is lignin or a lignin containing material.

19. The method of claim 15, which further comprises contacting the substrate with an enhancing agent.

* * * * *